(12) United States Patent
Matsuo et al.

(10) Patent No.: US 8,080,239 B2
(45) Date of Patent: Dec. 20, 2011

(54) COSMETIC

(75) Inventors: Ayano Matsuo, Yokohama (JP); Akio Nasu, Yokohama (JP); Katsunori Yoshida, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 1201 days.

(21) Appl. No.: 11/794,775

(22) PCT Filed: Jan. 13, 2006

(86) PCT No.: PCT/JP2006/300329
§ 371 (c)(1),
(2), (4) Date: Jul. 5, 2007

(87) PCT Pub. No.: WO2006/075679
PCT Pub. Date: Jul. 20, 2006

(65) Prior Publication Data
US 2010/0004201 A1    Jan. 7, 2010

(30) Foreign Application Priority Data

Jan. 17, 2005   (JP) .................................. 2005-009013
Jun. 1, 2005    (JP) .................................. 2005-160799

(51) Int. Cl.
| *A61Q 1/00* | (2006.01) |
| *A61Q 1/06* | (2006.01) |
| *A61Q 1/10* | (2006.01) |
| *A61Q 1/12* | (2006.01) |
| *A61Q 5/00* | (2006.01) |
| *A61Q 5/02* | (2006.01) |

(52) U.S. Cl. ........... 424/78.03; 424/59; 424/64; 424/69; 424/70.1; 424/70.7; 424/70.12; 424/401

(58) Field of Classification Search ........................ None
See application file for complete search history.

(56) References Cited

FOREIGN PATENT DOCUMENTS

| EP | 1496080 A1 * | 1/2005 |
| JP | 04-211605 A | 8/1992 |
| JP | 04-234307 A | 8/1992 |
| JP | 05-112423 A | 5/1993 |
| JP | 05-112424 A | 5/1993 |
| JP | 05-262616 A | 10/1993 |
| JP | 06-157236 A | 6/1996 |
| JP | 09-071504 A | 3/1997 |
| JP | 09-194594 A | 7/1997 |
| JP | 09-249518 A | 9/1997 |
| JP | 09-278892 A | 10/1997 |
| JP | 10-316540 A | 12/1998 |
| JP | 11-263706 A | 9/1999 |
| JP | 2000-219608 A | 8/2000 |
| JP | 2005-042097 A | 2/2005 |
| JP | 05-025280 A | 2/2010 |
| JP | 2003-146832 A | 5/2010 |
| JP | 05-247414 A | 9/2010 |
| JP | 2000-262883 A | 9/2010 |
| WO | 97/45097 A1 | 12/1997 |
| WO | 02051939 A1 | 7/2002 |
| WO | 2004/024798 A1 | 3/2004 |
| WO | 2006075679 A1 | 7/2006 |

* cited by examiner

*Primary Examiner* — Jyothsna Venkat
(74) *Attorney, Agent, or Firm* — Townsend & Banta

(57) ABSTRACT

The present invention provides a cosmetic that contains glycerin modified on both ends with silicone represented by the following general formula (a).

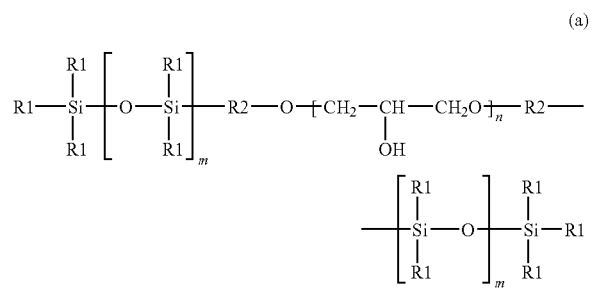

(a)

In this formula, R1 denotes a straight chain or branched alkyl group having 1-12 carbon atoms or phenyl group, R2 denotes an alkylene group having 2-11 carbon atoms, m is 10-120, and n is 1-11.

The object of the present invention is to provide a cosmetic that contains glycerin modified on both ends with silicone and is superior in terms of the sensation during use and the powder dispersion stability.

24 Claims, 3 Drawing Sheets

[FIG. 1]
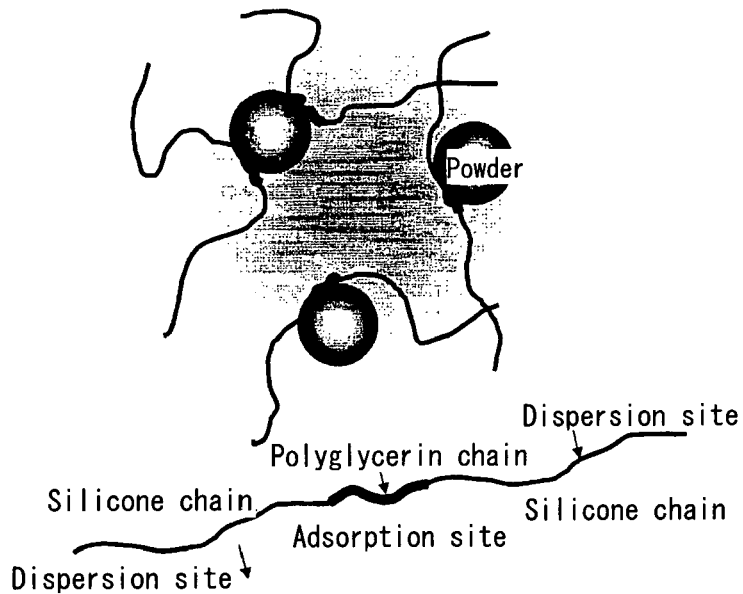
[FIG. 2]
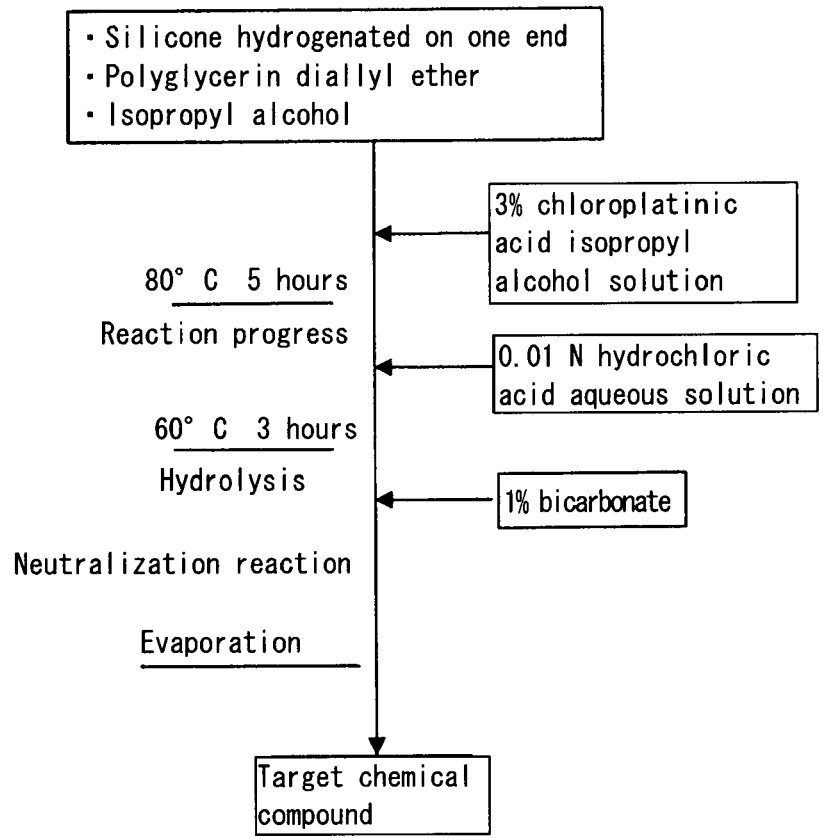

[FIG. 3]
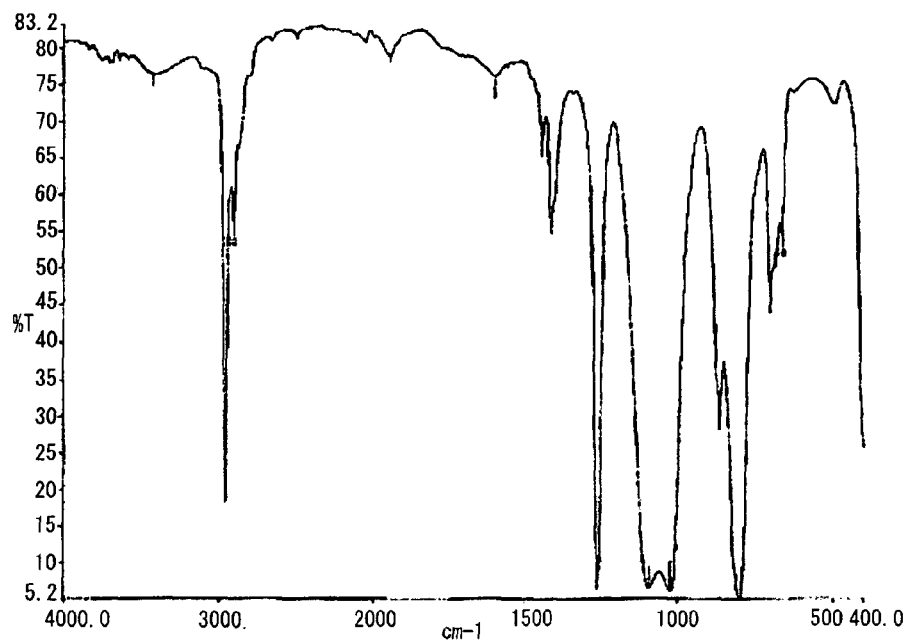
[FIG. 4]
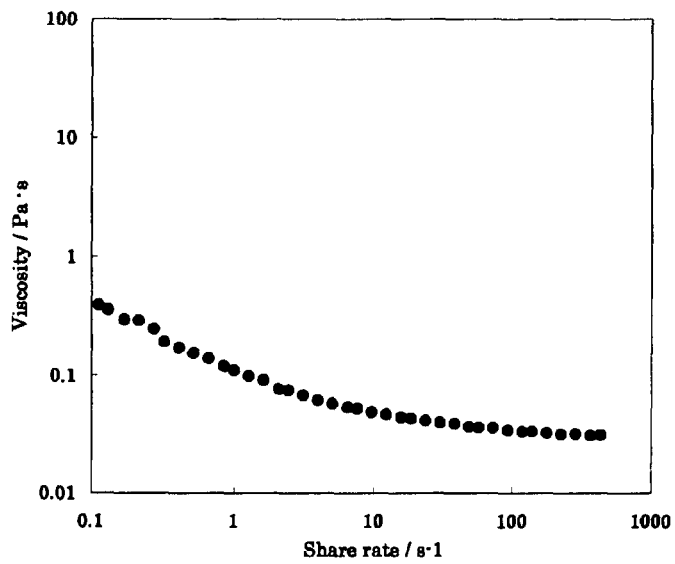

[FIG. 5]
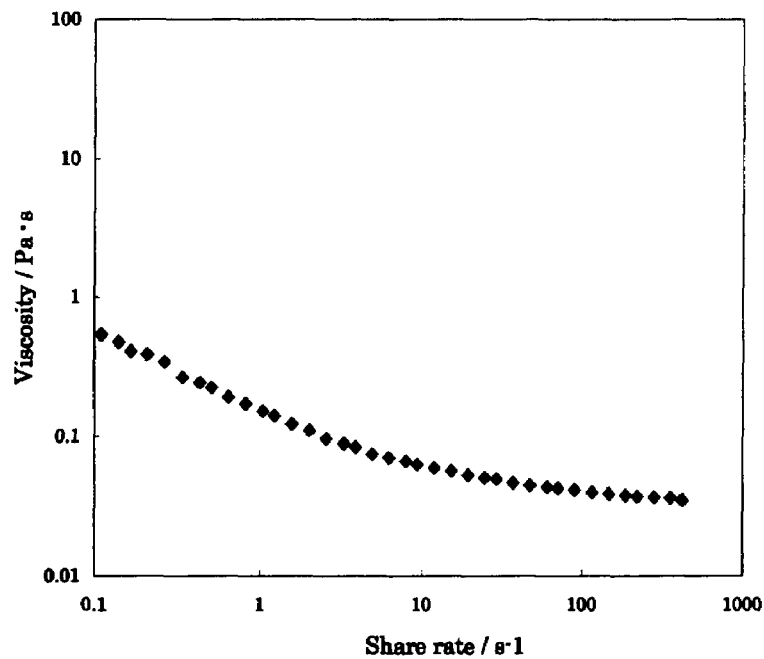
[FIG. 6]
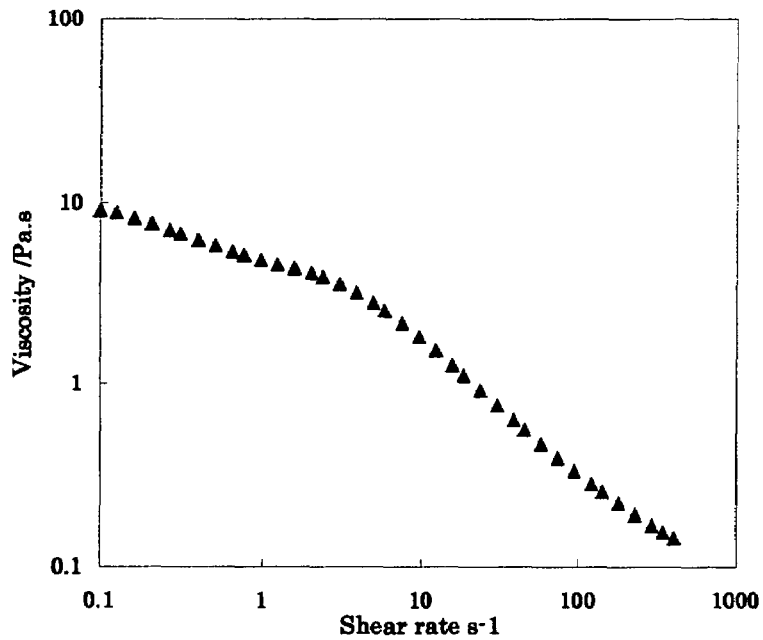

COSMETIC

TECHNICAL FIELD

The present invention relates to a cosmetic containing glycerin modified on both ends with silicone having a specific structure.

BACKGROUND ART

Silicone oil is blended in many cosmetics as an oil component that gives a refreshing sensation. For example, alkyl-modified silicone (Patent Document 1), fluorine-modified silicone (Patent Document 2), cholesterol-modified silicone (Patent Document 3), acylalkylimine-modified silicone (Patent Document 4), glyceryl-modified silicone (Patent Document 5), alkylglyceryl ether-modified silicone (Patent Document 6), and alkylmonoglyceryl ether-fluorine-modified silicone (Patent Document 7) are blended in cosmetics.

However, since silicone oil gives a strong refreshing sensation and leaves a squeaky sensation of the skin, silicone oil having a texture that feels natural on the skin has been strongly desired.

On the other hand, water-in-oil type emulsified compositions having the oil phase as the outer phase and the water phase as the inner phase are used in various cosmetics. Such water-in-oil type emulsified compositions are, compared with the oil-in-water type, superior in terms of protecting the skin, making the skin supple, and suppressing moisture evaporation from the skin, and therefore are considered to be a suitable formulation for endermic liniments.

Examples of emulsifiers made from a water-in-oil type emulsified composition that have been used traditionally include lipophilic surfactants having a HLB of approximately 1-12, such as polyhydric alcohol fatty acid ester type surfactants such as glycerin fatty acid esters and sorbitan fatty acid esters, as well as polyoxyalkylene-modified organopolysiloxane type surfactants (Non-patent document 1).

However, the water-in-oil type emulsified compositions using these emulsifier have poor emulsification stability and separation between the water phase and the oil phase occurs at high temperatures or over time, making it very difficult to stabilize the formulation.

Also, a method in which wax is blended into the oil phase, i.e. the outer phase, to stabilize the formulation is also being used. However, since wax melts or softens at higher temperatures, there is a problem in that the stability of the formulation is not sufficient. Also, there is a new problem in terms of usability in that spreadability is poor and stickiness occurs at the time of application.

Also, many cosmetics into which powder is blended, such as sunscreens and foundations, require water resistance and/or antiperspiration properties, and therefore hydrophobicized powder is often times blended into a W/O type formulation.

However, when a large quantity of powder is blended into a W/O type formulation, there are problems in that the increased viscosity due to aggregation of powder causes poor spreading at the time of application and the skin turns whiter after the application. To deal with these problems, a technique to more stably disperse powder in an oil agent has been developed.

Technology to primarily disperse powder has been advancing by using miniaturizers such as roller mills, beads mills, and high pressure homogenizers; however, how to keep finely dispersed powder dispersed and free of aggregation for a long time is an issue. Many cosmetics contain silicone oil as an oil component and therefore patents have been filed related to powder dispersing agents using modified silicone. For example, Patent Document 8 uses a powder-in-oil dispersion that uses a dispersing agent prepared by copolymerizing (A) organopolysiloxane monomers and (B) monomers having polylactone-containing groups, hydroxyl groups, or anionic groups. In Patent Document 9, ultraviolet blocking fine particles are dispersed by using a silicone-type dispersing agent composed of modified silicone or reactive silicone.

Patent Document 10 discloses an inorganic powder-in-oil dispersing agent composed of fatty acids to which alkylene oxide is added; dispersibility and stability of POE (4.5) lauryl ether acetic acid, POE (4) stearyl ether acetic acid, POE (10) lauryl ether acetic acid, POE (12) stearyl ether acetic acid, and sodium POE (10) lauryl ether acetate are verified in the examples.

[Patent Document 1] Japanese Patent Laid-Open H5-262616
[Patent Document 2] Japanese Patent Laid-Open H5-247214
[Patent Document 3] Japanese Patent Laid-Open H5-25280
[Patent Document 4] Japanese Patent Laid-Open H5-112423
[Patent Document 5] Japanese Patent Laid-Open H6-157236
[Patent Document 6] Japanese Patent Laid-Open H5-112424
[Patent Document 7] Japanese Patent Laid-Open H9-249518
[Patent Document 8] Japanese Patent Laid-Open H11-263706
[Patent Document 9] Domestic re-publication of PCT international patent publication WO97/45097
[Patent Document 10] Japanese Patent Laid-Open 2000-262883
[Non-Patent Document 1] "Oil Chemistry Handbook—Lipid and Surfactant" 4th edition, 2001, edited by Japan Oil Chemists' Society, Maruzen Corporation

DISCLOSURE OF INVENTION

Technical Problem

In view of the aforementioned view points, the inventors conducted earnest research and discovered that using glycerin modified on both ends with silicone having a specific structure for an oil component makes it possible to obtain oil-in-water type emulsified compositions, water-in-oil type emulsified cosmetics, oil based cosmetics, and cosmetics that are refreshing and at the same time absorbed well into the skin, and also to obtain cosmetics having superior dispersibility of the powder, thus completing the present invention.

The object of the present invention is to provide a cosmetic that is refreshing and also absorbed into the skin well when used.

Technical Solution

That is, the present invention provides a cosmetic that characteristically contains glycerin modified on both ends with silicone represented by the following general formula (a).

[Chemical formula 1]

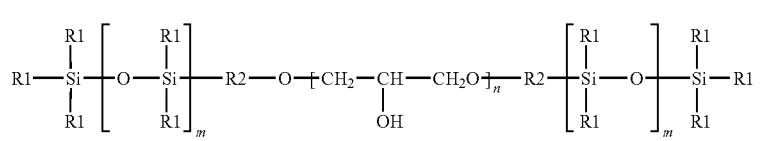

(a)

In this formula, R1 denotes a straight chain or branched alkyl group having 1-12 carbon atoms or a phenyl group, R2 denotes an alkylene group having 2-11 carbon atoms, m is 10-120, and n is 1-11.

Also, the present invention provides the aforementioned cosmetic wherein said cosmetic is an oil based cosmetic.

Furthermore, the present invention provides the aforementioned cosmetic wherein said cosmetic is a water-in-oil type emulsified cosmetic.

Also, the present invention provides the aforementioned cosmetic wherein said cosmetic is an oil-in-water type emulsified cosmetic.

Furthermore, the present invention provides the aforementioned cosmetic wherein said cosmetic additionally contains powder.

Advantageous Effects (1) The cosmetic of the present invention contains glycerin modified on both ends with silicone as an oil component and therefore is absorbed into the skin very well and yet is refreshing.
(2) The glycerin modified on both ends with silicone used in the present invention exhibits a superior emulsifying function toward water-in-oil type emulsified compositions. As a result, a water-in-oil type emulsified composition that has superior stability and gives a superior sensation during use can be provided without substantially adding a surfactant.
(3) Also, in the case of oil-in-water type emulsified cosmetics, an emulsified composition having superior stability and usability can be obtained by additionally using a prior art hydrophilic emulsifier.
(4) The cosmetic of the present invention has very high dispersion stability and provides a stable powder dispersion cosmetic. Stability of the powder is particularly high in oil containing silicone oil FIG. 1 illustrates the powder dispersion stability. The aforementioned glycerin modified on both ends with silicone, as a powder dispersion stabilizer, has dispersion sites made of silicone chains on either side and therefore it allows the polymers to disperse in the dispersion medium solvent while it holds powder on the adsorption site made of a highly adsorptive polyglycerin chain; and this is believed to be the reason why it exhibits a very prominent dispersion stabilizing effect.
(5) The glycerin modified on both ends with silicone used in the present invention can exhibit varied HLB and viscosity in a cosmetic by choosing appropriate molecular weights for the dimethylpolysiloxane chain and the polyglycerin chain. As a result, a cosmetic that gives a desired sensation during use can be designed.

BRIEF DESCRIPTION OF DRAWINGS

FIG. 1 illustrates the powder dispersion stability of the glycerin modified on both ends with silicone used in the present invention.

FIG. 2 illustrates the synthesis scheme for the glycerin modified on both ends with silicone, obtained by means of ether bonding.

FIG. 3 is an IR spectrum of the glycerin modified on both ends with silicone of Synthesis example 1.

FIG. 4 shows Theological measurements with varied shearing rates for the powder dispersion composition using the glycerin modified on both ends with silicone of Synthetic example 1.

FIG. 5 shows Theological measurements with varied shearing rates for the powder dispersion composition using the glycerin modified on both ends with silicone of Synthetic example 2.

FIG. 6 shows Theological measurements with varied shearing rates for the powder dispersion composition using the polyether-modified glycerin of Comparative example.

BEST MODE FOR CARRYING OUT THE INVENTION

The basic structure of the glycerin modified on both ends with silicone used in the present invention is a BAB triblock copolymer; for example, silicone having a hydrogen residue on one end, represented by the following structure (c), can be used for B. In general formula (a), R1's can be either identical to each other or different. Also, R2's can be either identical to each other or different.

A denotes a glycerin residue.

The silicone having hydrogen on one end having the following structure (c) is a prior art chemical compound. A BAB tri-block copolymer having any degree of polymerization can be prepared by using a prior art method.

[Chemical formula 2]

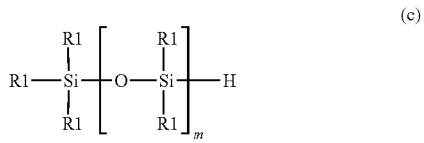

(c)

In this formula, each R1 is a straight chain or branched alkyl group or a phenyl group, and m denotes a number 10-120. R1's can be either identical to each other or different.

Although the bond between A and B is not an essential structure for the present invention, the glycerin modified on both ends with silicone shown in the present invention is prepared by bonding compound (c) and a compound represented by the following structural formula (d) by means of ether bonding using a platinum catalyst.

[Chemical formula 3]

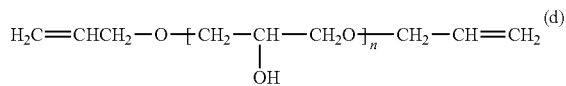

(d)

In this formula, n denotes a number 1-11.

A BAB tri-block copolymer can be synthesized by means of a prior method. The synthesis scheme is shown in FIG. 2. The glycerin modified on both ends with silicone represented by the following structural formula (a) {preferably structural formula (b)} can be thus obtained.

[Chemical formula 4]

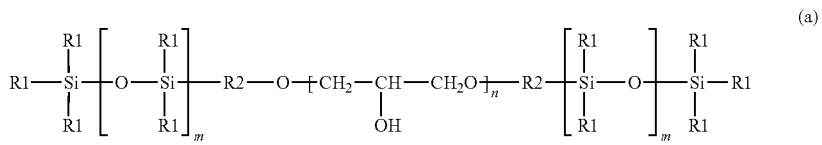

(a)

In this formula, R1 denotes a straight chain or branched alkyl group having 1-12 carbon atoms or a phenyl group, R2 denotes an alkyl group having 2-11 carbon atoms, m denotes a number 10-120, and n denotes a number 1-11.

[Chemical formula 5]

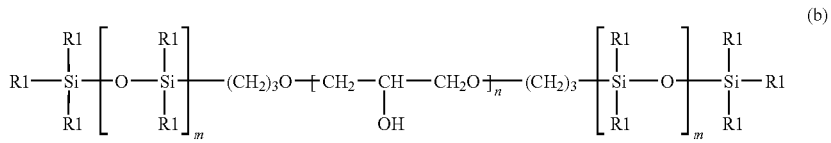

(b)

In this formula, each R1 denotes a straight chain or branched alkyl group or a phenyl group, m denotes a number 10-120, and n denotes a number 1-11.

The degree of polymerization of the silicone chains, m, is preferably 10-120. The side chain substituent is preferably a methyl group, but a phenyl or other alkyl can be the substituent as well.

The degree of polymerization of the glycerin chains, n, is preferably 1-11.

For the glycerin modified on both ends with silicone to function well, as shown in FIG. 1, the solubility of the B block in the solvent and a high adsorption level of the A block chains onto the powder surface are important. That is, the hydrophilicity/hydrophobicity balance (HLB) of the A and B blocks needs to be in the appropriated range for proper functioning. The HLB can be obtained by using a prior art method; for example, it can be calculated by using Griffin's formula (HLB value=Glycerin portion molecular weight×20/total molecular weight). In the present invention, the HLB should preferably be 0.2-3.0.

The spread of the A block chains, which prevent aggregation of powder particles to each other, depends on the molecular weight of the polymer; the higher the molecular weight of the A block chains, the stronger the aggregation prevention effect. Adsorption of the B block chains onto the powder particles is believed to occur through weak interactions such as the van der Waals' force and hydrogen bonding. However, the use of polyglycerin for the B block chains provides stronger adsorption compared with polyethylene glycol and such, and therefore a sufficient adsorption level can be achieved with a relatively low molecular weight. When the molecular weight of the A and B blocks becomes too high, the cosmetic sometimes becomes hard to spread and/or resists spreading when applied. As described above, there is an appropriate range of molecular weight; the molecular weight should preferably be 2,000-20,000.

The blend ratio of the glycerin modified on both ends with silicone used in the present invention is determined as deemed appropriate. Usually, it is 0.1-50 wt %, preferably 0.1-30 wt %, of the total amount of the cosmetic.

In the case of a cosmetic that contains powder and silicone oil, the blend ratio is 0.1-30 wt % of the total amount of the powder, the silicone oil, and the glycerin modified on both ends with silicone.

In addition to the glycerin modified on both ends with silicone that is blended in as an oil component, the cosmetic of the present invention can contain other oil components. The present invention is preferably used for oil based cosmetics.

Preferable are one, two or more oil components chosen from a group consisting of chain polysiloxanes such as dimethylpolysiloxane and methylphenyl polysiloxane, cyclic polysiloxanes such as octamethylcyclotetrasiloxane and decamethylcyclopentasiloxane, modified silicones such as polyether-modified silicone, alkyl-modified silicone, and epoxy-modified silicone, and silicone resins such as trimethoxysiloxy silicic acid and high polymer methylpolysiloxane.

The silicone dispersion medium can contain other oil components as long as the effect of the present invention is not adversely affected. The oil components that can be blended in include liquid paraffin, solid paraffin, petrolatum, ceresin, isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl hydroxy 12-stearate, di2-ethylene glycol ethylhexanoate, dipentaerythritol fatty acid ester, n-alkylene glycol monoisostearate, neopentyl glycol dicaprate, diisostearyl malate, glyceryl di2-heptylundecanoate, trimethylolpropane tri2-ethylhexanoate, trimethylolpropane triisostearate, tetra2-pentaerythritol ethylhexanoate, glycerin tri2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyl decyl palmitate, 2-hexyl decyl adipate, diisopropyl sebacate, 2-ethylhexyl succinate, triethyl citrate, avocado oil, tsubaki oil, macademia nut oil, corn oil, olive oil, rapeseed oil, sesame oil, wheat germ oil, sasanqua oil, castor oil, linseed oil, safflower oil, cotton seed oil, soybean oil, peanut oil, grape seed oil, almond oil, tea seed oil, rice bran oil, jojoba oil, meadow foam oil, and germ oil.

Also, the aforementioned glycerin modified on both ends with silicone functions as an excellent emulsifier for water-in-oil emulsified cosmetics. Therefore, the present invention can provide a water-in-oil type emulsified cosmetic that has superior emulsification stability and usability. The blend ratio of the glycerin modified on both ends with silicone that functions as the emulsifier is not limited in particular. Usually, the blend ratio is 0.1-10.0 wt % of the water-in-oil type emulsified cosmetic. The preferable blend ratio range is 0.5-5.0 wt %. If the blend ratio is less than 0.1 wt %, then the emulsification stability can be poor. No improvement in the effect is observed when it is more than 10.0 wt %. Other emulsifiers can be additionally used in the water-in-oil type emulsified composition of the present invention; however, the glycerin modified on both ends with silicone alone can essentially enable a stable emulsified cosmetic.

In the case of oil-in-water type emulsified cosmetics, an emulsified composition having superior stability and usability can be obtained by using the aforementioned glycerin modified on both ends with silicone along with a prior art hydrophilic emulsifier. The blend ratio of the aforementioned glycerin modified on both ends with silicone is usually 0.1-30 wt % of the total amount of the oil phase of the oil-in-water type emulsified cosmetic (the total amount of the powder dispersed in the oil phase and the oil component that constitutes the oil phase). The blend ratio of the hydrophilic emulsifier is not limited in particular. Usually, the blend ratio is 0.1-10.0 wt % of the oil-in-water type emulsified cosmetic.

The present invention adds the aforementioned glycerin modified on both ends with silicone to a cosmetic and thus improves its powder dispersibility and emulsification stability. Ingredients that are usually used in cosmetics and medical drugs can be added to the cosmetic of the present invention within the range that does not affect the effect of the invention; and the cosmetic can be manufactured using a conventional method.

Selection of the oil component blended into the water-in-oil type emulsified composition and the oil-in-water type emulsified composition is not limited in particular. The blend ratio of the oil component is not limited; it is chosen as appropriate. Usually, it is 10-95 wt %, preferably 20-80 wt %, for a water-in-oil type emulsified cosmetic and 5-70 wt %, preferably 10-30 wt %, for an oil-in-water type emulsified cosmetic. The cosmetic of the present invention is prepared by using a conventional method after mixing the essential ingredients.

Since the cosmetic of the present invention is superior in terms of the powder dispersibility, it is preferably used as a powder-containing cosmetic. Selection of the powder to be dispersed is not limited in particular. Inorganic powder (titanium oxide or zinc oxide in particular) is preferable. The dispersion stability is very high even for a mixed powder of both, which is a characteristic of the present invention.

The average particle size of the powder is preferably 0.5-150 nm.

Here, if the titanium oxide or zinc oxide powder is blended in as an ultraviolet scattering agent, fine particles having an average particle size of 1-50 nm are preferable.

The powder blended into the cosmetic of the present invention can be treated on the surface to improve the dispersion stability of the powder.

The cosmetic of the present invention that contains powder can be prepared by mechanically dispersing the powder, the glycerin modified on both ends with silicone, and the silicone type dispersion medium.

For the preliminary kneading/mixing and dispersion treatment, a suitable dispersing apparatus can be used, with heating if necessary. According to the viscosity of the slurry to be prepared, a dispersing apparatus such as a roller mill, high pressure homogenizer, or beads mill can be selected and used.

For the powder to be dispersed in the aforementioned cosmetics, an ultraviolet scattering agent can be preferably used. Examples of the ultraviolet scattering agent include inorganic powders such as titanium oxide and zinc oxide, or surface-coated inorganic powder prepared by coating the surface of said inorganic fatty acid ester with a fatty acid soap such as aluminum stearate and zinc palmitate, a fatty acid such as stearic acid, myristic acid, and palmitic acid, and a fatty acid ester such as dextrin palmitate.

One, two or more types of the aforementioned ultraviolet scattering agents can be selected and blended in. The blend ratio of the ultraviolet scattering agent is 0.1-50.0 wt %, preferably 1.0-40.0 wt %, of the cosmetic. If the blend ratio of the ultraviolet scattering agent is too low, then the ultraviolet protection effect may not be sufficient; if it is too high, then the emulsion may not be obtained. The cosmetic of the present invention manifests an excellent effect in that the ultraviolet scattering agent powder is dispersed very well.

The applications of the cosmetic of the present invention are not limited in particular. For example, it can be used for various products including lotions, emulsions, creams, foundations, lipsticks, cleansing foams, shampoos, hair rinses, lip creams, hair sprays, hair foams, sunscreen creams, tanning creams, eye liners, mascaras, nail creams, and body makeup cosmetics.

EXAMPLES

The invention is described in specific detail through Examples. The present invention is not limited to these Examples. The blend ratios are in relation to the total amount and in weight-percentage units unless specified otherwise.

Synthesis Example 1

Synthesis of Glycerin Modified on Both Ends with Silicone 100 g of dimethylpolysiloxane hydrogenated on one end (Mw=app. 4,600) represented by formula (e), 3.5 g of triglycerin diallyl ether, and 100 g of isopropyl alcohol are put into a reaction vessel, to which 0.05 g of an isopropyl alcohol solution of 3% chloroplatinic acid is added, followed by 5 hours of reaction at 80° C. 1.5 g of a 0.01N HCl aqueous solution is added and hydrolysis is carried out for three hours at 60° C., followed by addition of 0.2 g of 1% sodium bicarbonate solution to neutralize the solution. The reaction solution is concentrated by means of evaporation to obtain the target compound in the form of a fluid viscous liquid.

[Chemical formula 6]

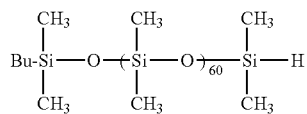

(e)

Synthesis Example 2

Synthesis of Glycerin Modified on Both Ends with Silicone 100 g of dimethylpolysiloxane hydrogenated on one end (Mw=app. 4,600) represented by formula (e), 4.3 g of tetraglycerin diallyl ether, and 100 g of isopropyl alcohol are put into a reaction vessel, to which 0.05 g of an isopropyl alcohol solution of 3% chloroplatinic acid is added, followed by 5 hours of reaction at 80° C. 1.5 g of a 0.01N HCl aqueous solution is added and hydrolysis is carried out for three hours at 60° C., followed by addition of 0.2 g of 1% sodium bicarbonate solution to neutralize the solution. The reaction solution is concentrated by means of evaporation to obtain the target compound in the form of a fluid viscous liquid.

[Chemical formula 7]

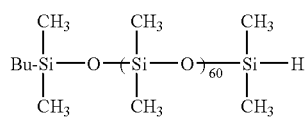

(e)

Synthesis Example 3

Synthesis of Glycerin Modified on Both Ends with Silicone 100 g of dimethylpolysiloxane hydrogenated on one end (Mw=app. 7,600) represented by formula (f), 2.6 g of tetraglycerin diallyl ether, and 100 g of isopropyl alcohol are put into a reaction vessel, to which 0.05 g of an isopropyl alcohol solution of 3% chloroplatinic acid is added, followed by 5 hours of reaction at 80° C. 1.5 g of a 0.01N HCl aqueous solution is added and hydrolysis is carried out for three hours at 60° C., followed by addition of 0.2 g of 1% sodium bicarbonate solution to neutralize the solution. The reaction solution is concentrated by means of evaporation to obtain the target compound in the form of a fluid viscous liquid.

[Chemical formula 8]

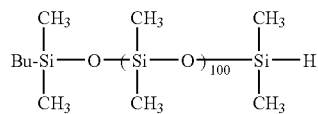

(f)

Synthesis Example 4

Synthesis of Glycerin Modified on Both Ends with Silicone 100 g of methylphenylpolysiloxane hydrogenated on one end (Mw=app. 5,600) represented by formula (f), 2.9 g of triglycerin diallyl ether, and 100 g of isopropyl alcohol are put into a reaction vessel, to which 0.05 g of an isopropyl alcohol solution of 3% chloroplatinic acid is added, followed by 5 hours of reaction at 80° C. 1.5 g of a 0.01N HCl aqueous solution is added and hydrolysis is carried out for three hours at 60° C., followed by addition of 0.2 g of 1% sodium bicarbonate solution to neutralize the solution. The reaction solution is concentrated by means of evaporation to obtain the target compound in the form of a fluid viscous liquid.

[Chemical formula 9]

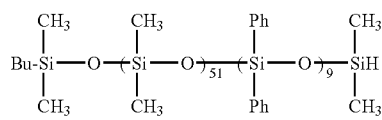

(g)

In this formula, Ph denotes a phenyl group.

Synthesis Example 5

Synthesis of Glycerin Modified on Both Ends with Silicone 100 g of methyldodecylpolysiloxane hydrogenated on one end (Mw=app. 5,900) represented by formula (h), 2.7 g of triglycerin diallyl ether, and 100 g of isopropyl alcohol are put into a reaction vessel, to which 0.05 g of an isopropyl alcohol solution of 3% chloroplatinic acid is added, followed by 5 hours of reaction at 80° C. 1.5 g of a 0.01N HCl aqueous solution is added and hydrolysis is carried out for three hours at 60° C., followed by addition of 0.2 g of 1% sodium bicarbonate solution to neutralize the solution. The reaction solution is concentrated by means of evaporation to obtain the target compound in the form of a fluid viscous liquid.

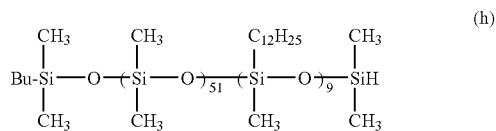

(h)

The synthesis scheme for the aforementioned Synthesis examples 1-5 is shown in FIG. 2. FIG. 3 shows an IR spectrum of Example 1. In this spectrum, peaks from polydimethylsiloxane are observed near 800, 1,000, 1,260, and 2,960 cm$^{-1}$, and peaks from the secondary alcohol in polyglycerin are observed near 1,400 cm$^{-1}$, indicating that the synthesis goes according to the scheme and the target compound is obtained.

"Evaluation of the Dispersion Stability"

<Preparation of the Dispersion>

38 g of fine particle powder, a dispersing agent prepared by using the method of Synthesis example 1 or Synthesis example 2, and 5 g of Comparative example are added to 57 g of silicone type dispersion medium, and glass beads (1 mm diameter) are added such that the weight ratio with the fine particle powder is 1:1, followed by one hour of mixing with a paint shaker to prepare a slurry-like dispersion. A dispersion is prepared in the same manner except for the fact that 5 g of the dispersing agent prepared by using the method of Comparative example 1 is used instead of the dispersing agent prepared in Synthesis example 1. For the powder to be dispersed, mixed powder of equal amounts of P1 and P2 are used.

Ingredients used are shown below.
(1) Fine Particle Powder (P1): Fine Particle Titanium Dioxide Treated with Fatty Acid Soap
    Product name: 100TV (from Teika Pharmaceutical Co., Ltd.)
    Particle size: Major axis approximately 0.03 μm, minor axis approximately 0.005 μm
    Aluminum myristate treatment amount: 10 wt %
(2) Fine Particle Powder (P2): Silicone-Treated Silica-Coated Zinc Oxide
    Product name: SS-Activox C80 (from Showa Denko K. K.)
    Particle size: approximately 0.03 μm
    Amount of silica treatment: 20 wt %
(3) Comparative Sample: Polyether-Modified Silicone
    Product name: Silicone KF6017 (from Shin-Etsu Chemical Co., Ltd.)
    Polyether-modification rate: 20% Molecular weight: approximately 6,000 HLB value: 4.0
(4) Dispersion Medium:
Decamethylcyclopentasiloxane
    Product name: KF-995 (from Shin-Etsu Chemical Co., Ltd.)<
<Evaluation of the Dispersion Properties>

Rheological measurement of the dispersion is carried out to evaluate the dispersion stability of each glycerin modified on both ends with Silicone.
(Evaluation Method)
Evaluation apparatus: Cone plate type viscometer AR1000-N from TA Instruments
Measurement conditions: 4 cm 4° Steel geometry
    Shearing rate: $0.1\ s^{-1}$-$500\ s^{-1}$ 25° C.
(Results)

The evaluation results of the dispersion using the glycerin modified on both ends with silicone of Synthetic example 1 are shown in FIG. 4.

The evaluation results of the dispersion using the glycerin modified on both ends with silicone of Synthetic example 2 are shown in FIG. 5.

The evaluation results of the dispersion using the polyether-modified silicone, i.e. Comparative example, is shown in FIG. 6.

When the dispersion stability of the powder in the dispersion is good, its fluid characteristics reflect the fluid characteristics of the dispersion medium silicone, and the behavior is Newtonian, i.e. the viscosity is nearly constant regardless of the magnitude of the shearing rate.

The behavior of the dispersion using the dispersing agent of Comparative example is shown in FIG. 6, in which the dispersion prepared by mixing titanium oxide (P1) and zinc oxide (P2) shows a significant increase in the viscosity in the low shearing rate region, indicating aggregation of the powder.

In contrast, the behavior of the dispersion using the dispersing agent synthesized in Synthetic example 1 and Synthetic example 2 is shown in FIG. 4, in which the dispersion prepared by mixing titanium oxide (P1) and zinc oxide (P2) shows virtually Newtonian fluid properties, indicating excellent dispersion stability. There have been very few reports of a dispersing agent that enables a dispersion using mixed powder (P1 and P2) to exhibit virtually Newtonian behavior; this indicates that the aforementioned dispersing agent has an excellent effect of improving the dispersion stability.

The aforementioned evaluation measurements indicate that the compounds of Synthetic examples 1 and 2 exhibit a superior effect of stabilizing dispersion. The compound of Synthetic example 3 exhibits the dispersion stability similar to that of Synthetic examples 1 and 2.

"Evaluation of the Dispersion Stability: Relationship Between HLB and Molecular Weight"

The powder dispersion properties of the glycerin modified on both ends with silicone and polyether-modified silicone that were synthesized in the same manner as Synthetic examples 1-3 and Comparative example were evaluated by means of rheological measurements as described above. The tables indicate that the glycerin modified on both ends with silicone used in the present invention exhibits superior dispersion properties.

TABLE 1

<Evaluation results for the powder dispersion stabilizer having a molecular weight of approximately 11,000>

| | Dispersion properties |
|---|---|
| Glycerin modified on both ends with silicone HLB value | |
| 0.1 | X |
| 0.15 | X |
| 0.2 | ◯ |
| 0.48 | ◯ |
| 1.4 | ◯ |
| 1.8 | ◯ |
| 2.0 | ◯ |
| 2.5 | ◯ |
| 2.8 | ◯ |
| 3.2 | Δ |
| 4.8 | X |
| Polyether-modified silicone HLB value | |
| 0.5 | X |
| 1.8 | X |
| 4.0 | X |

Dispersion properties
◯: Good, Δ: Reasonably good, X: Not good

TABLE 2

<Evaluation results for the powder dispersion stabilizer having a HLB value of 0.5>

| | Dispersion properties |
|---|---|
| Glycerin modified on both ends with silicone Molecular weight | |
| 1000 | X |
| 1500 | Δ |
| 2000 | ◯ |
| 3000 | ◯ |
| 5000 | ◯ |
| 9000 | ◯ |
| 12000 | ◯ |
| 15000 | ◯ |
| 20000 | ◯ |
| 25000 | X |
| 31000 | X |

TABLE 2-continued

<Evaluation results for the powder dispersion
stabilizer having a HLB value of 0.5>

| Polyether-modified silicone Molecular weight | Dispersion properties |
|---|---|
| 6000 | X |
| 11000 | X |
| 15000 | X |

Dispersion properties
○: Good, Δ: Reasonably good, X: Not good

Next, the emulsification stability test was carried out for water-in-oil type cream containing the aforementioned glycerin modified on both ends with silicone as an emulsifier and water-in-oil type cream containing a conventional emulsifier. The compositions of the water-in-oil type creams and the results are shown in the following Table 3. As for typical conventional water-in-oil type emulsifiers, diglyceryl diisostearate was used in Comparative example 1 and POE (3) hydrogenated castor oil was used in Comparative example 2. 2-ethylhexyl paramethoxycinnamate (IOB 0.28) and 2-ethylhexyl succinate (IOB 0.32) were added as polar oil-based ingredients.

(1) Stability Over Time (after One Month)

The water-in-oil type creams of the Examples and the Comparative examples were kept at room temperature for a month, after which the appearance of the emulsion was visually (or by using an optical microscope) observed.

<Evaluation Criteria>

◉: Particles were homogeneous and the emulsification state was good.
○: Particles were somewhat uneven, but the emulsification state was good.
Δ: Particles became coarse and separation of the water phase and the oil phase was observed.
x: The water phase and the oil phase was completely separated.

(2) Temperature Stability (50° C.)

The water-in-oil type creams of the Examples and the Comparative examples were kept at 50° C. for a month, after which the appearance of the emulsion was visually (or by using an optical microscope) observed. The evaluation criteria are as follows:

<Evaluation Criteria>

◉: Particles were homogeneous and the emulsification state was very good.
○: Particles were nearly homogeneous and the emulsification state was good.
Δ: Particles were somewhat uneven and slight separation of the water phase and the oil phase was observed.
x: The water phase and the oil phase was completely separated.

TABLE 3

|  | Example A | Comparative example 1 | Comparative example 2 |
|---|---|---|---|
| Polyglycerin modified on both ends with silicone from Synthesis example 1 | 2.5 | — | — |
| Diglyceryl diisostearate | — | 2.5 | — |
| POE (3) hydrogenated castor oil | — | — | 2.5 |
| Ion-exchanged water | Balance | Balance | Balance |
| Polyethylene glycol | 1.0 | 1.0 | 1.0 |
| 1.3-butylene glycol | 5.0 | 5.0 | 5.0 |
| Preservative | Appropriate amount | Appropriate amount | Appropriate amount |
| Decamethylcyclopentasiloxane | 12.0 | 12.0 | 12.0 |
| 2-ethylhexyl paramethoxycinnamate | 10.0 | 10.0 | 10.0 |
| Di-2-ethylhexyl succinate | 2.0 | 2.0 | 2.0 |
| Stability over time (one month) | ◉ | Δ | Δ |
| Temperature stability (50° C.) | ◉ | Δ | Δ |

The above Table 3 indicates that Example A of the present invention is far superior to Comparative examples 1 and 2 that use conventional water-in-oil type emulsifiers in terms of stability over time and temperature stability of the emulsified composition.

Cosmetics containing glycerin modified on both ends with silicone are shown below.

Example 1

Mascara

| (Formulation) | (wt %) |
|---|---|
| Light isoparaffin | 7 |
| Compound of Synthesis example 1 | 2 |
| Decamethylcyclopentasiloxane | 10 |
| Trimethylsiloxysilicic acid | 10 |
| Methylpolysiloxane emulsion | Appropriate amount |
| 1,3-butylene glycol | 4 |
| Polyethylene glycol dioleate | 2 |
| Diglyceryl diisostearate | 2 |
| DL-α-tocopherol acetate | 0.1 |
| Paraoxybenzoic ester | Appropriate amount |
| Black iron oxide | 7 |
| Seaweed extract | 0.1 |
| Bentonite | 1 |
| Dimethyl distearyl ammonium hectorite | 6 |
| Poly vinyl acetate emulsion | 30 |
| Purified | Balance |

(Evaluation)

The obtained mascara had good gloss and superior color development.

Example 2

Mascara

| (Formulation) | (wt %) |
|---|---|
| Light isoparaffin | Balance |
| Decamethylcyclopentasiloxane | 8 |
| Compound of Synthesis example 2 | 3 |
| Trimethylsiloxysilicic acid | 8 |
| Polyoxyethylene-methylpolysiloxane copolymer | 2 |
| 1,3-butylene glycol | 2 |
| Macadamia nut oil | 1 |
| Polyoxyethylene hydrogenated castor oil | 2 |

-continued

| (Formulation) | (wt %) |
|---|---|
| triisostearate | |
| Acrylic resin-coated aluminum powder | 4 |
| Dimethyl distearyl ammonium hectorite | 5 |
| Dextrin palmitate | 2 |
| Purified water | 2 |

(Evaluation)

The obtained mascara had good gloss and superior color development.

Example 3

Mascara

| (Formulation) | (wt %) |
|---|---|
| Light isoparaffin | Balance |
| Methylhydrogenpolysiloxane | 1 |
| Decamethylcyclopentasiloxane | 10 |
| Compound of Synthesis example 1 | 5 |
| Castor oil | 2 |
| Candelilla wax | 5 |
| Isostearic acid | 3 |
| Oleic acid | 1 |
| Glyceryl tri-2-ethylhexanoate | 2 |
| Sapindaceae extract | 0.1 |
| Wild oat extract | 0.1 |
| Dextrin palmitate | 13 |
| Trimethylsiloxysilicic acid | 15 |
| Tetradecene | 0.1 |
| Polyethylene | 5 |
| Microcrystalline wax | 5 |

(Evaluation)

The obtained mascara had good gloss and superior color development.

Example 4

Mascara

| (Formulation) | (wt %) |
|---|---|
| Light isoparaffin | Balance |
| Compound of Synthesis example 3 | 3 |
| Decamethylcyclopentasiloxane | 5 |
| Octyl palmitate | 1 |
| Isostearic acid | 1 |
| Microcrystalline wax | 1 |
| Carnauba wax | 2 |
| Beeswax | 2 |
| Dextrin (palmitate/octanoate) | 15 |
| Fatty acid ester mixed with sucrose (Cosmelike MX-10 from Dai-ichi Kogyo Seiyaku Co., Ltd.) | 20 |
| Sucrose tetraisostearate (Crodesta 4-IS from Croda Japan KK) | 10 |
| Trimethylsiloxysilicic acid | 5 |
| Aluminum stearate | 1 |
| Silicone-coated pigment (iron oxide) | 0.5 |
| Silicone-coated pigment (titanium oxide) | 0.3 |
| Silicone-coated pigment (red iron oxide) | 0.2 |
| Barium sulfate | 0.1 |
| Red iron oxide-coated mica | Appropriate amount |
| δ-tocopherol | 0.1 |

(Evaluation)

The obtained mascara had good gloss and superior color development.

Example 5

Lipstick

| (Formulation) | (wt %) |
|---|---|
| Methylphenylpolysiloxane | 5 |
| Non-water based polymer emulsion (*) | 30 |
| Fluorine-modified methylphenylpolysiloxane | 25 |
| Decamethylcyclopentasiloxane | 5 |
| Compound of Synthesis example 4 | 5 |
| Dimethylpolysiloxane | Balance |
| Polyoxyethylene-modified silicone | 5 |
| Glycerin | 3 |
| Pigment | 5 |
| Ceresin | 10 |
| Candelilla wax | 2 |
| Aerosil R972 (from Degussa) | 1 |
| Spherical silica | 0.5 |
| δ-tocopherol | 0.05 |
| Octylmethoxy cinnamate | 0.5 |
| Laponite | 0.3 |

(*) 15% of Methyl methacrylate monomer, 25% of ethyl acrylate monomer, 0.1% of polymerization initiator, and 5% of dispersion stabilizer dimethylpolysiloxane graft polymer (molecular weight approximately 150,000) were added to 54.9% of the dispersion medium decamethylcyclopentasiloxane and stirred for 10 hours at 120° C. for polymerization; monomers were then removed by reducing the pressure and the temperature was cooled down to 25° C. to obtain non-water based polymer dispersion that has milky white appearance and an average dispersed polymer particle size of 1 μm wherein volatile silicone is used as a dispersion medium.

(Evaluation)

The obtained lipstick had a moist texture and yet was not too sticky, giving a good tactile sensation during use.

Example 6

Lipstick

| (Formulation) | (wt %) |
|---|---|
| Ceresin | 6 |
| Decamethylcyclopentasiloxane | Balance |
| Compound of Synthesis example 5 | 5 |
| Polyoxyethylene/methylpolysiloxane copolymer (MW = 6,000) | 5 |
| "Non-water based dispersion prepared by dispersing alkyl acrylate/tris (trimethylsiloxy) silylpropyl methacrylate in decamethylcyclopentasiloxane" | 30 |
| Dimethylsiloxane/diphenylsiloxane/methyl (perfluoroalkyl) siloxane | 20 |
| Methylphenylpolysiloxane | 5 |
| Stearoxymethylpolysiloxane | 2 |
| Candelilla wax | 4 |
| Silylated silicic acid anhydride | 1 |
| Silicone-coated pigment (red iron oxide, titanium oxide, etc.) | 7 |
| Red iron oxide-coated titanated mica | 5 |
| Mica | 1 |
| Dye | Appropriate amount |
| Silicic acid anhydride | 2 |
| Titanium oxide | 3 |
| Poly (oxyethylene/oxypropylene)/methylpolysiloxane copolymer (MW = 50,000) | 2 |
| Perfume | Appropriate amount |

(Evaluation)

The obtained lipstick had gloss and a moist texture and yet was not too sticky, giving a good tactile sensation during use.

Example 7

Lipstick

| (Formulation) | (wt %) |
| --- | --- |
| A-olefin oligomer | 5 |
| Methylphenylpolysiloxane | 5 |
| Compound of Synthesis example 1 | 2 |
| Diisostearyl malate | Balance |
| Heavy liquid isoparaffin | 25 |
| Pigment | 7 |
| Glycerin | 1 |
| 1,3-butylene glycol | 3 |
| Calcium chloride | 0.1 |
| Sodium acetylated hyaluronate | 0.02 |
| 2-ethylhexyl paramethoxycinnamate | 2 |
| Synthetic sodium/magnesium silicate | 1.5 |
| Dextrin palmitate | 2.5 |
| Polyoxyethylene-methylpolysiloxane copolymer | 0.5 |
| Purified water | 1 |
| Perfume | Appropriate amount |

(Evaluation)

The obtained lipstick had a moist texture and yet was not too sticky, giving a good tactile sensation during use.

Example 8

Solid Powdery Foundation

| (Formulation) | (wt %) |
| --- | --- |
| Dimethyl polysiloxane | 5 |
| Compound of Synthesis example 1 | 2 |
| Isostearic acid | 0.5 |
| Diisostearyl malate | 3 |
| Glyceryl tri-2-ethylhexanoate | 1 |
| Sorbitan sesquiisostearate | 1 |
| Spherical PMMA-coated mica | 6 |
| PRISMTONE POWDER YR | 1 |
| Fine particle zinc oxide | 0.5 |
| Fine particle titanium oxide | 2 |
| Synthetic phlogopite | 2 |
| Metal soap-treated talc | 8 |
| Spherical silica | 5 |
| Vitamin E acetate | 0.1 |
| δ-tocopherol | 0.1 |
| Ethylparaben | Appropriate amount |
| Methylbis (trimethylsiloxy) silylisopentyl trimethoxycinnamate | 1 |
| 2-ethylhexyl paramethoxycinnamate | 3 |
| Spherical poly alkyl acrylate powder | 6 |
| Methylhydrogenpolysiloxane-coated talc | Balance |
| Methylhydrogenpolysiloxane-coated sericite | 20 |
| Methylhydrogenpolysiloxane-coated titanium oxide | 15 |
| Methylhydrogenpolysiloxane-coated pigment (coloring agent) | 5 |

(Evaluation)

The obtained lipstick-type solid powdery foundation exhibited superior color development and felt very smooth on the skin.

Example 9

Solid Powdery Foundation

| (Formulation) | (wt %) |
| --- | --- |
| Synthesized hydrocarbon wax particles | 2 |
| Dimethyl polysiloxane | 6 |
| Purified lanolin | 5 |
| Compound of Synthesis example 4 | 5 |
| Glyceryl tri-2-ethylhexanoate | 2 |
| Sorbitan sesquiisostearate | 0.5 |
| Acicular fine particle titanium oxide | 5 |
| Fine particle zinc oxide | 1 |
| Silicone-coated sintered iron oxide/titanium oxide | 7 |
| Barium sulfate | 8 |
| Calcined sericite | Balance |
| Titanium-reduced mica titanium pearl pigment | 2 |
| Silicone-coated synthetic phlogopite | 5 |
| Silicone-coated talc | 2 |
| Spherical silica | 3 |
| Silicone-coated mica | 15 |
| Stearyl glycyrrhizate | 0.1 |
| Ascorbyl dipalmitate | 0.1 |
| DL-α-tocopherol acetate | 0.1 |
| D-δ-tocopherol | 0.1 |
| Paraoxybenzoic ester | Appropriate amount |
| 2-ethylhexyl paramethoxycinnamate | 3 |
| Silicone-coated red iron oxide | 1 |
| Silicone-coated yellow iron oxide | 1 |
| Silicone-coated black iron oxide | 1 |
| Spherical poly alkyl acrylate | 3 |
| Perfume | Appropriate amount |

Example 10

Solid Powdery Foundation

| (Formulation) | (wt %) |
| --- | --- |
| Silicone-treated sericite | 15 |
| Silicone-treated mica | 20 |
| Silicone-treated synthetic mica | 10 |
| Silicone-treated talc | Balance |
| Zinc oxide | 2 |
| Methylsiloxane network polymer spherical powder | 4 |
| Boron nitride | 3 |
| Zinc myristate | 2 |
| Crushed liquid titanated mica | 3 |
| Silicone-treated titanium oxide | 10 |
| Silicone-treated iron oxide | 4 |
| Silicone-treated zinc oxide | 5 |
| Dimethyl polysiloxane | 4 |
| Compound of Synthesis example 1 | 2 |
| 2-ethylhexyl paramethoxycinnamate | 3 |
| Polyoxyethylene/alkyl co-modified silicone | 1 |
| Sorbitan sesquiisostearate | 1 |
| Paraben | Appropriate amount |
| δ-tocopherol | Appropriate amount |
| Perfume | Appropriate amount |

(Preparation Method and Evaluation)

The powder components, the oil components, and the crushed liquid titanated mica in the formulation were dispersed/mixed in ethyl alcohol by using a sand grinder mill having 3 mm-diameter zirconia beads. After distilling ethyl alcohol, the mixture was crushed once with a pulverizer; it was then packed in a container (mid-sized plate made of resin) and dry-molded with a prior art method to obtain a solid powdery foundation. The obtained solid powdery foundation exhibited a superior smoothness.

Example 11

Solid Powdery Foundation

| (Formulation) | (wt %) |
| --- | --- |
| Methyl (N-propyl-pyrrolidone carboxylate) siloxane/methylpolysiloxane copolymer | 5 |
| Compound of Synthesis example 1 | 5 |
| Dimer dilinoleic acid (phytosteryl/behenyl) | 5 |
| Glycerin tri-2-ethylhexanoate | 3 |
| Methylpolysiloxane | 2 |
| Sorbitan sesquiisostearate | 1 |
| Pearl pigment (product name: Timiron MP115) | 40 |
| Mica | 10 |
| Yellow iron oxide | 2 |
| Talc | Balance |

(Preparation Method and Evaluation)

The powder ingredients were mixed using a Henschel mixer and such, to which the oil based ingredients were added, followed by homogeneous mixing, to obtain a cosmetic base agent. To this 60-70 wt % of ethanol was added and mixed homogeneously to obtain a slurry. Since the oil based ingredients would be partially lost by ethanol removal, an increased amount of 120-160%, as necessary, was initially added so that the end product would have the blend ratios as specified in the formulation. This was poured into a medium plate and pressure-molded by using a molding head (molding pressure 20 kg) and simultaneously ethanol was suctioned out through the back side of the molding head. After the suction, the molded product was dried for two hours at 50° C. The slurry obtained in the preparation process had an increased fluidity, which improved the productivity.

Example 12

Foundation

| (Formulation) | (wt %) |
| --- | --- |
| Dimethyl polysiloxane | 3 |
| Decamethylcyclopentasiloxane | 10 |
| Compound of Synthesis example 1 | 5 |
| Polyoxyethylene-methylpolysiloxane copolymer | 3 |
| Dodecamethylcyclohexasiloxane | 5 |
| Glycerin | 4 |
| 1,3-butylene glycol | 5 |
| Palmitic acid | 0.5 |
| Stearyltrimethylammonium chloride | 0.2 |
| Metal soap-treated talc | 2 |
| Cross-linked silicone powder (Trefil E-506) | 0.1 |
| Red iron oxide-coated titanated mica | 0.5 |
| N-lauroyl-L-lysine | 2 |
| Tocopherol acetate | 0.1 |
| δ-tocopherol | 0.1 |
| Paraoxybenzoic ester | Appropriate amount |
| Phenoxyethanol | 0.2 |
| Spherical nylon powder | 1 |
| Spherical poly alkyl acrylate powder | 3 |
| Sweet clover extract | 2 |
| Purified water | Balance |
| Dextrin fatty acid-treated talc | 3 |
| Dextrin fatty acid-treated titanium oxide | 15 |
| Dextrin fatty acid-treated yellow iron oxide | 3 |
| Dextrin fatty acid-treated black iron oxide | 0.5 |

(Preparation Method and Evaluation)

The oil based ingredients and the water based ingredients in the formulation were each heated and dissolved completely. The oil phase was added to the water phase and emulsified by using an emulsifying apparatus. The emulsion was cooled by a heat exchanger to obtain a cream. The obtained foundation had superior smoothness and was not sticky, giving a good sensation during use.

Example 13

Foundation

| (Formulation) | (wt %) |
| --- | --- |
| Dimethyl polysiloxane | 15 |
| Decamethylcyclopentasiloxane | 20 |
| Compound of Synthesis example 5 | 5 |
| Polyoxyethylene-methylpolysiloxane copolymer | 5 |
| High molecular weight amino-modified silicone | 0.1 |
| Glycerin | 5 |
| 1,3-butylene glycol | 10 |
| Palmitic acid | 0.5 |
| Macadamia nut oil fatty acid cholesteryl ester | 0.1 |
| Stearyltrimethylammonium chloride | 0.2 |
| Alkyl-modified silicone resin-coated yellow iron oxide | 2 |
| Alkyl-modified silicone resin-coated red iron oxide | 1 |
| Alkyl-modified silicone resin-coated black iron oxide | 0.3 |
| Alkyl-modified silicone resin-coated titanium oxide | 10 |
| Alkyl-modified silicone resin-coated talc | 1.5 |
| Silicone-coated spindle-shaped titanium oxide | 3 |
| DL-α-tocopherol acetate | 0.1 |
| Paraoxybenzoic ester | Appropriate amount |
| Methylbis (trimethylsiloxy) silylisopentyl trimethoxycinnamate | 0.1 |
| Dimethyl distearyl ammonium hectorite | 1.5 |
| Spherical nylon powder | 1 |
| Purified water | Balance |
| Perfume | Appropriate amount |

(Preparation Method and Evaluation)

The oil based ingredients and the water based ingredients in the formulation were each heated and dissolved completely. The oil phase was added to the water phase and emulsified by using an emulsifying apparatus. The emulsion was cooled by a heat exchanger to obtain cream. The obtained foundation had superior smoothness and was not sticky, giving a good sensation during use.

Example 14

Rinse

| (Formulation) | (wt %) |
| --- | --- |
| Dimethyl polysiloxane | 2 |
| Compound of Synthesis example 2 | 2 |
| Stearyl alcohol | 2 |
| Behenyl alcohol | 1 |
| Glycerin | 1.5 |
| Octyl palmitate | 1 |
| Polyoxyethylene stearyl ether | 0.2 |
| Citric acid | 0.05 |
| Paraoxybenzoic ester | Appropriate amount |
| phenoxyethanol | Appropriate amount |
| Hydroxyethylcellulose | 0.1 |
| Stearyltrimethylammonium chloride | 1 |
| High polymer methylpolysiloxane | 1.5 |
| Purified water | Balance |
| Perfume | Appropriate amount |

(Preparation Method and Evaluation)

The aforementioned ingredients were mixed with a conventional method to obtain a hair rinse. The obtained rinse was not sticky or squeaky, and improved the smoothness of the hair.

Example 15

Rinse

| (Formulation) | (wt %) |
| --- | --- |
| Dimethyl polysiloxane | 15 |
| Compound of Synthesis example 4 | 5 |
| High polymer dimethylpolysiloxane | 1 |
| Cetanol | 4.5 |
| Glycerin | 10 |
| Cetyl 2-ethylhexanoate | 2 |
| Stearyltrialkylammonium chloride | 1.5 |
| Stearyltrimethylammonium chloride | 0.3 |
| Citric acid | 0.01 |
| Tocopherol acetate | 0.05 |
| Paraoxybenzoic ester | Appropriate amount |
| Phenoxyethanol | Appropriate amount |
| Hydroxyethylcellulose | 0.05 |
| Purified water | Balance |
| Perfume | Appropriate amount |

(Preparation Method and Evaluation)

The aforementioned ingredients were mixed with a conventional method to obtain a hair rinse. The obtained rinse was not sticky or squeaky, and improved the smoothness of the hair.

Example 16

Rinse

| (Formulation) | (wt %) |
| --- | --- |
| Dimethyl polysiloxane | 0.5 |
| Compound of Synthesis example 5 | 0.5 |
| Benzyl alcohol | 5 |
| Cetostearyl alcohol | 7 |
| Behenyl alcohol | 3 |
| Self-emulsified glycerin monostearate | 1 |
| Sodium N-stearoyl-N-methyltaurate | 1 |
| Citric acid | 0.2 |
| Phenoxyethanol | Appropriate amount |
| Purified water | Balance |
| Perfume | Appropriate amount |

(Preparation Method and Evaluation)

The aforementioned ingredients were mixed with a conventional method to obtain a hair rinse. The obtained rinse gave a good tactile sensation and also improved the smoothness of the hair.

Example 17

Hair Shampoo

| (Formulation) | (wt %) |
| --- | --- |
| Dimethyl polysiloxane | 1.5 |
| Compound of Synthesis example 3 | 0.5 |
| Dipropylene glycol | 3 |
| Ethylene glycol distearate | 2 |
| Cocoyl monoethanolamide | 2 |
| Sodium lauroyl methyltaurate | 0.1 |
| Sodium polyoxyethylenelaurylethersulfate | 7.5 |
| Triethanolamine polyoxyethylenelaurylethersulfate | 3.5 |
| Cocoyl amidepropyl betaine | 3.5 |
| Marcoat 550 (from Cargon) | 7.5 |
| Citric acid | 0.01 |
| Sodium L-glutamate | 0.2 |
| Sodium chloride | 1 |
| Sodium benzoate | Appropriate amount |
| Disodium edetate | Appropriate amount |
| Sodium hydroxide | 0.01 |
| Purified water | Balance |
| Perfume | Appropriate amount |

<Preparation Method and Evaluation>

The aforementioned ingredients were mixed with a conventional method to obtain a hair shampoo. The obtained hair shampoo exhibited superior hair texture when used to wash hair.

Example 18

Hair Shampoo

| (Formulation) | (wt %) |
| --- | --- |
| Dimethyl polysiloxane | 0.1 |
| Compound of Synthesis example 1 | 0.1 |
| High polymer dimethylpolysiloxane | 0.15 |
| Ethylene glycol distearate | 2.5 |
| Cocoyl diethanolamide | 6 |
| Sodium dodecane-1,2-diol acetate ether | 1.5 |
| Sodium methyl cocoyl taurate | 7.5 |
| Cocoyl amidepropyl betaine | 5 |
| Polymer JR-400 (from Union Carbide) | 0.1 |
| Dimethyldiallylammonium chloride-acrylamide copolymer | 1 |

-continued

| (Formulation) | (wt %) |
|---|---|
| Citric acid | 0.7 |
| Sodium chloride | 0.7 |
| Phenoxyethanol | Appropriate amount |
| Sodium benzoate | Appropriate amount |
| Disodium edetate | Appropriate amount |
| Purified water | Balance |
| Perfume | Appropriate amount |

<Preparation Method and Evaluation>

The aforementioned ingredients were mixed with a conventional method to obtain a hair shampoo. The obtained hair shampoo exhibited a superior smooth hair texture when used to wash hair and gave gloss to the hair after drying.

Example 19

Rinse in Shampoo

| (Formulation) | (wt %) |
|---|---|
| Dimethylpolysiloxane 2 | 1 |
| Compound of Synthesis example 2 | |
| Polyoxyethylene-methylpolysiloxane copolymer | 2 |
| Cetanol | 0.5 |
| Polyoxyethylene hydrogenated castor oil | 4 |
| Ethylene glycol distearate | 2 |
| Cocoyl diethanolamide | 7 |
| Sodium polyoxyethylenelaurylethersulfate | 5 |
| Triethanolamine polyoxyethylenelaurylethersulfate | 2.5 |
| Sodium lauroylmethyl-beta-alanine | 1 |
| Sodium methyl cocoyl taurate | 4 |
| Betaine lauryldimethylaminoacetate | 5 |
| Polymer JR-400 (from Union Carbide) | 0.4 |
| Stearyltrimethylammonium chloride (25%) | 0.1 |
| Citric acid | 0.4 |
| Sodium benzoate | Appropriate amount |
| Disodium edetate | Appropriate amount |
| Purified water | Balance |
| Perfume | Appropriate amount |

<Preparation Method and Evaluation>

The aforementioned ingredients were mixed with a conventional method to obtain a rinse-in-shampoo. The obtained hair shampoo exhibited a superior smooth hair texture when used to wash hair and gave gloss to the hair after drying.

Example 20

Cleansing Oil

| (Formulation) | (wt %) |
|---|---|
| Ion-exchanged water | 4 |
| Glycerin | 1 |
| Glyceryl PEG (8) isostearate | 35 |
| Liquid paraffin | Balance |
| Glyceryl triisooctanoate | 5 |
| Isoparaffin | 5 |
| Dimethylpolysiloxane (6 mPa · s) | 3 |
| Compound of Synthesis example 4 | 1 |
| Pentaerythrityl tetraoctanoate | 3 |
| Squalane | 3 |
| Methylphenylpolysiloxane | 3 |
| Ascorbic acid glucoside | 0.1 |

(Preparation Method and Evaluation)

The cleansing oil was obtained by mixing and dissolving***. The obtained cleansing oil was smooth and non-sticky and gave no squeaky sensation after rinsing, providing a good tactile sensation during use.

Example 21

Cleansing Oil

| (Formulation) | (wt %) |
|---|---|
| Liquid petrolatum | 73 |
| Dimethylpolysiloxane | 2 |
| Compound of Synthesis example 2 | 1 |
| Ethanol | 0.3 |
| Isostearic acid | 0.5 |
| Lauric acid | 0.1 |
| Cetyl 2-ethylhexanoate | 10 |
| PEG-12 diisostearate | 4 |
| PEG-8 diisostearate | 1 |
| PEG-10 diisostearate | 3 |
| Vitamin E | 0.1 |
| Purified water | Balance |

(Preparation Method and Evaluation)

The cleansing oil was obtained by mixing and melting. The obtained cleansing oil was smooth and non-sticky and gave no squeaky sensation after rinsing, providing a good tactile sensation during use.

Example 22

Hair Spray

| (Formulation) | (wt %) |
|---|---|
| Volatile isoparaffin | 14 |
| Dimethylpolysiloxane | 3 |
| Compound of Synthesis example 1 | 5 |
| Ethanol | Appropriate amount |
| Purified water | 2 |
| High polymer dimethylsiloxane-methyl (aminopropyl) siloxane copolymer | 4 |
| Poly (oxyethylene-oxypropylene)-methylpolysiloxane copolymer | 4 |
| Perfume | Appropriate amount |
| Mother solution/propellant = 40/60 (L. P. G MPa) | 0.115 |

(Preparation Method and Evaluation)

After mixing and dissolving the ingredients, an aerosol spray was prepared using the above composition ratio. The hair sprayed with the obtained hair spray had reduced stickiness after application and a smooth and good tactile sensation.

Example 23

Hair Cream

| (Formulation) | (wt %) |
|---|---|
| Dimethylpolysiloxane | 5 |
| Compound of Synthesis example 5 | 10 |
| Polyoxyethylene-methylpolysiloxane copolymer | 0.2 |
| Ethanol | 10 |
| Propylene glycol | 5 |
| 2-amino-2-methyl-1-propanol | Appropriate amount |
| Trisodium edetate | Appropriate amount |
| Xanthan gum | 0.1 |
| Vinyl acetate-vinyl pyrrolidone copolymer | 0.5 |
| Alkyl acrylate/methacrylate copolymer | 0.2 |
| Carboxyvinyl polymer | 0.4 |
| High polymer dimethylsiloxane-methyl (aminopropyl) siloxane copolymer | 0.5 |
| High polymer dimethylpolysiloxane | 1 |
| Purified water | Balance |
| Perfume | Appropriate amount |

(Evaluation)

This hair cream exhibited a superior effect of giving suppleness to the hair.

Example 24

Hair Cream

| (Formulation) | (wt %) |
|---|---|
| Volatile isoparaffin | 10 |
| Dimethylpolysiloxane | 1 |
| Compound of Synthesis example 2 | 1 |
| Ethanol | 10 |
| 1,3-butylene glycol | 5 |
| Isostearic acid | 0.5 |
| Polyoxyethylene hydrogenated castor oil | 0.1 |
| 2-alkyl-N-carboxymethyl-N-hydroxyethylimidazolium betaine | 1 |
| Sodium hydroxide | 0.3 |
| High polymer methylpolysiloxane | 2 |
| Carboxyvinyl polymer | 0.8 |
| Paraoxybenzoic ester | Appropriate amount |
| Trisodium edetate | Appropriate amount |
| Purified water | Balance |
| Perfume | Appropriate amount |

Example 25

Hair Cream

| (Formulation) | (wt %) |
|---|---|
| Liquid paraffin | 5 |
| Petrolatum | 2 |
| Dimethylpolysiloxane | 3 |
| Compound of Synthesis example 4 | 3 |
| Cetanol | 4 |
| Stearyl alcohol | 1 |
| 1,3-butylene glycol | 10 |
| Polyoxypropylene glyceryl ether | 2 |
| Polyoxyethylene glyceryl ethylene isostearate | 2 |
| Lipophilic glycerin monostearate | 2 |
| Polymer Example-400 | 0.5 |
| Paraoxybenzoic ester | Appropriate amount |
| Purified water | Balance |
| Perfume | Appropriate amount |

(Evaluation)

This hair cream exhibited a superior effect of giving suppleness to the hair.

Example 26

Hair Mousse

| (Formulation) | (wt %) |
|---|---|
| Ethanol | 10 |
| Propylene glycol | 5 |
| Lauric diethanolamide | 0.2 |
| Alkyltrimethylammonium chloride (77%) | 0.1 |
| Yukaformer SM | 10 |
| Polyoxyethylene-methylpolysiloxane copolymer | 1 |
| Volatile isoparaffin | 5 |
| High polymer dimethylpolysiloxane | 1 |
| Compound of Synthesis example 4 | 1 |
| Purified water | Balance |
| Perfume | Appropriate amount |
| Mother solution/propellant = 40/60 (L.P.G MPa) | 0.43 |

(Preparation Method and Evaluation)

The water based ingredients and the oil based ingredients were separately mixed and dissolved; the oil phase was then added to the water phase and emulsified with a homogenizer. The obtained emulsion was made into an aerosol formulation by using the above composition ratio. The obtained hair mousse was smooth and not rough, and exhibited good usability.

Example 27

Wax Mousse

| (Formulation) | (wt %) |
|---|---|
| Liquid paraffin | 6 |
| Dimethylpolysiloxane | 5 |
| Compound of Synthesis example 3 | 3 |
| Glycerin | 8 |
| Propylene glycol | 8 |
| Butylethylpropanediol | 0.5 |
| Jojoba oil | 1 |
| Carnauba wax | 5 |
| Isostearic acid | 0.5 |
| Polyoxyethylene hydrogenated castor oil | 0.5 |
| Polyoxyethylene behenyl ether | 5 |
| 2-alkyl-N-carboxymethyl-N-hydroxyethylimidazolium betaine | 8 |

-continued

| (Formulation) | (wt %) |
|---|---|
| Phenoxyethanol | 0.5 |
| High polymer dimethylpolysiloxane | 0.5 |
| Purified water | Balance |
| Perfume | Appropriate amount |
| Mother solution/propellant = 90/10 (L.P.G MPa) | 0.43 |

(Evaluation)

This wax mousse gave a good non-sticky and smooth tactile sensation during use.

Example 28

Wax

| (Formulation) | (wt %) |
|---|---|
| Liquid paraffin | 10 |
| Petrolatum | 5 |
| Microcrystalline wax | 5 |
| Stearyl alcohol | 2 |
| Propylene glycol | 10 |
| Carnauba wax | 3 |
| Isostearic acid | 1 |
| Stearic acid | 2 |
| Compound of Synthesis example 5 | 1 |
| Pentaerythritol tetra-2-ethylhexanoate | 3 |
| Polyoxyethylene glyceryl ethylene isostearate | 1 |
| Self-emulsified glycerin monostearate | 2 |
| Kaolin | 5 |
| Silicic acid anhydride | 2 |
| Triethanolamine | 0.3 |
| Sodium metaphosphate | Appropriate amount |
| Paraoxybenzoic ester | Appropriate amount |
| Xanthan gum | 0.1 |
| Bentonite | 1 |
| Purified water | Balance |
| Perfume | Appropriate amount |

(Evaluation)

This wax mousse gave a good non-sticky tactile sensation during use.

Example 29

Hair Oil

| (Formulation) | (wt %) |
|---|---|
| Hydrogenated polyisobutene | Balance |
| Ethanol | 10 |
| Oxybenzone | Appropriate amount |
| High polymer methylpolysiloxane | 10 |
| Compound of Synthesis example 4 | 2 |

(Preparation Method and Evaluation)

The hair oil was obtained by mixing and melting. The obtained hair oil was non-sticky and gave good gloss to the hair.

Example 30

Emulsion

| (Formulation) | (wt %) |
|---|---|
| Dimethylpolysiloxane | 2 |
| Compound of Synthesis example 1 | 1 |
| Behenyl alcohol | 1 |
| Batyl alcohol | 0.5 |
| Glycerin | 5 |
| 1,3-butylene glycol | 7 |
| Erythritol | 2 |
| Hydrogenated oil | 3 |
| Squalane | 6 |
| Pentaerythritol tetra-2-ethylhexanoate | 2 |
| Polyoxyethylene glyceryl ethylene isostearate | 1 |
| Polyoxyethyleneglycerin monostearate | 1 |
| Potassium hydroxide | Appropriate amount |
| Sodium hexametaphosphate | 0.05 |
| Phenoxyethanol | Appropriate amount |
| Carboxyvinyl polymer | 0.1 |
| Purified water | Balance |

(Preparation Method and Evaluation)

A conventional method was used to prepare the emulsion. The obtained emulsion was refreshing and at the same time gave a smooth and good tactile sensation.

Example 31

Emulsion

| (Formulation) | (wt %) |
|---|---|
| Liquid paraffin | 7 |
| Petrolatum | 3 |
| Decamethylcyclopentasiloxane | 1 |
| Compound of Synthesis example 5 | 1 |
| Behenyl alcohol | 1 |
| Glycerin | 5 |
| Dipropylene glycol | 7 |
| Polyethylene glycol 1500 | 2 |
| Jojoba oil | 1 |
| Isostearic acid | 0.5 |
| Stearic acid | 0.5 |
| Behenic acid | 0.5 |
| Pentaerythritol tetra-2-ethylhexanoate | 3 |
| Cetyl 2-ethylhexanoate | 3 |
| Glyceryl monostearate | 1 |
| Polyoxyethyleneglyceryl monostearate | 1 |
| Potassium hydroxide | 0.1 |
| Sodium hexametaphosphate | 0.05 |
| Stearyl glycyrrhizate | 0.05 |
| L-arginine | 0.1 |
| Royal jelly extract | 0.1 |
| Yeast extract | 0.1 |
| Tocopherol acetate | 0.1 |
| Sodium acetylated hyaluronate | 0.1 |
| Edetate trisodium | 0.05 |
| 4-tert butyl-4'-methoxybenzoylmethane | 0.1 |
| 2-ethylhexyl-p-methoxycinnamate | 0.1 |
| Carboxyvinyl polymer | 0.15 |
| Paraben | Appropriate amount |
| Purified water | Balance |
| Perfume | Appropriate amount |

(Preparation Method and Evaluation)

A conventional method was used to prepare the emulsion. The obtained emulsion was refreshing and at the same time gave a smooth and good tactile sensation.

Example 32

Protector

| (Formulation) | (wt %) |
|---|---|
| Dimethylpolysiloxane | 2 |
| Decamethylcyclopentasiloxane | 20 |
| Compound of Synthesis example 4 | 5 |
| Dodecamethylcyclohexasiloxane | 10 |
| Polyoxyethylene-methylpolysiloxane copolymer | 1.5 |
| Trimethylsiloxysilicic acid | 1 |
| 1,3-butylene glycol | 5 |
| Squalane | 0.5 |
| Talc | 5 |
| Dipotassium glycyrrhizinate | 0.1 |
| Tocopherol acetate | 0.1 |
| Edetate trisodium | 0.05 |
| 4-tert butyl-4'-methoxybenzoylmethane | 1 |
| 2-ethylhexyl-p-methoxycinnamate | 5 |
| Glyceryl diparamethoxycinnamate mono-2-ehtylhexanoate | 1 |
| Silicone-coated fine particle titanium oxide (40 nm) | 4 |
| Dimethyl distearyl ammonium hectorite | 0.5 |
| Spherical polyethylene powder | 3 |
| Phenoxyethanol | Appropriate amount |
| Purified water | Balance |
| Perfume | Appropriate amount |

(Preparation Method and Evaluation)

The oil phase and the water phase were each mixed and dissolved. Dispersion of the powder in the oil phase was thoroughly conducted, to which the water phase was added, and emulsification was done using a homogenizer. The obtained protector was highly transparent and exceptionally refreshing.

Example 33

Protector

| (Formulation) | (wt %) |
|---|---|
| Dimethylpolysiloxane | 2 |
| Compound of Synthesis example 2 | 2 |
| Methylphenylpolysiloxane | 2 |
| Ethanol | 5 |
| Glycerin | 4 |
| Dipropylene glycol | 5 |
| 1,3-butylene glycol | 5 |
| 2-ethylhexyl succinate | 3.5 |
| Potassium hydroxide | 0.1 |
| Sodium hexametaphosphate | 0.1 |
| Thiotaurine | 0.1 |
| Edetate trisodium | 0.1 |
| 4-tert butyl-4'-methoxybenzoylmethane | 3 |
| 2-ethylhexyl-paramethoxycinnamate | 3 |
| Iron oxide | 0.01 |
| Alkyl acrylate/methacrylate copolymer (Pemulen TR-2) | 0.1 |
| Carboxyvinyl polymer | 0.2 |
| Paraben | Appropriate amount |
| Purified water | Balance |
| Perfume | Appropriate amount |

(Preparation Method and Evaluation)

The oil phase and the water phase were each mixed and dissolved. The oil phase was added to the water phase, followed by emulsification by means of a homogenizer. The obtained protector was highly transparent and exceptionally refreshing.

Example 34

Lotion

| (Formulation) | (wt %) |
|---|---|
| Dimethylpolysiloxane | 0.5 |
| Compound of Synthesis example 3 | 0.5 |
| Ethanol | 3 |
| Behenyl alcohol | 0.3 |
| Glycerin | 5 |
| Dipropylene glycol | 5 |
| Erythritol | 1 |
| Polyethylene glycol 4000 | 1 |
| Squalane | 0.4 |
| Cetyl 2-ethylhexanoate | 0.1 |
| Sodium N-stearoyl-L-glutamate | 0.2 |
| Magnesium chloride | 0.1 |
| Arginine chloride | 0.1 |
| Hypotaurine | 0.1 |
| Edetate trisodium | 0.1 |
| Paraben | Appropriate amount |
| Purified water | Balance |
| Perfume | Appropriate amount |

(Evaluation)

This lotion gave a good, smooth tactile sensation.

Example 35

Cream

| (Formulation) | (wt %) |
|---|---|
| Dimethylpolysiloxane | 3 |
| Compound of Synthesis example 1 | 10 |
| Decamethylcyclopentasiloxane | 15 |
| Trimethylsiloxysilicic acid | 1 |
| Polyoxyethylene-methylpolysiloxane copolymer | 2 |
| Glycerin | 1 |
| 1,3-butylene glycol | 5 |
| Squalane | 1 |
| Titanium oxide | 1 |
| Talc | 2 |
| Aluminum stearate | 0.5 |
| Oil soluble licorice extract | 0.5 |
| 3 Na edetate | Appropriate amount |
| Paraben | Appropriate amount |
| Phenoxyethanol | Appropriate amount |
| Dimethyl distearyl ammonium hectorite | 0.8 |
| Spherical nylon powder | 1 |
| Purified water | Balance |

(Preparation Method and Evaluation)

The oil phase and the water phase were each mixed and dissolved. The water phase was added to the oil phase, followed by emulsification by means of a homogenizer. This cream gave a good, smooth tactile sensation.

Example 36

Cream

| (Formulation) | (wt %) |
|---|---|
| Stearic acid | 10 |
| Compound of Synthesis example 5 | 1 |
| Stearyl alcohol | 4 |
| Butyl stearate | 8 |
| Monoglyceryl stearate | 2 |
| Vitamin E acetate | 0.5 |
| Vitamin A palmitate | 0.1 |
| Macadamia nut oil | 1 |
| Perfume | Appropriate amount |
| Glycerin | 4 |
| 1,2-pantendiol | 3 |
| Sodium hyaluronate | 1 |
| Potassium hydroxide | 2 |
| Magnesium ascorbate phosphate | 0.1 |
| L-arginine hydrochloride | 0.01 |
| Edetate trisodium | 0.05 |
| Purified water | Balance |

(Preparation Method and Evaluation)

The oil phase and the water phase were separately heated up to 70° C. and completely dissolved. The oil phase was added to the water phase and emulsified by using an emulsifying apparatus. The emulsion was cooled by a heat exchanger to obtain cream. The obtained cream had superior smoothness and was not sticky, giving a good sensation during use.

Example 37

Sunscreen

| (Formulation) | (wt %) |
|---|---|
| Decamethylcyclopentasiloxane | 15 |
| Compound of Synthesis example 2 | 5 |
| Trimethylsiloxysilicic acid | 1 |
| Polyoxyethylene-methylpolysiloxane copolymer | 2 |
| Dipropylene glycol | 4 |
| Squalane | 5 |
| Silicone-coated fine particle titanium oxide (20 nm) | 10 |
| Talc (hydrophobicized) | 6 |
| Paraben | Appropriate amount |
| Phenoxyethanol | Appropriate amount |
| 4-tert butyl-4'-methoxybenzoylmethane | 0.1 |
| 2-ethylhexyl-p-methoxycinnamate | 7 |
| Glyceryl diparamethoxycinnamate mono-2-ehtylhexanoate | 0.5 |
| Spherical polyethylene powder | 5 |
| Dimethyl distearyl ammonium hectorite | 1 |
| Purified water | Balance |
| Perfume | Appropriate amount |

(Preparation Method and Evaluation)

The oil phase and the water phase were each mixed and dissolved. Dispersion of the powder in the oil phase was thoroughly conducted, to which the water phase was added, and emulsification was done using a homogenizer. The obtained sunscreen was highly transparent and exceptionally refreshing.

Example 38

Gel

| (Formulation) | (wt %) |
|---|---|
| Dimethylpolysiloxane | 3 |
| Compound of Synthesis example 3 | 2 |
| Glycerin | 2 |
| 1,3-butylene glycol | 5 |
| Polyethylene glycol 1500 | 3 |
| Polyethylene glycol 20000 | 3 |
| Cetyl octanoate | 3 |
| Citric acid | 0.01 |
| Sodium citrate | 0.1 |
| Sodium hexametaphosphate | 0.1 |
| Dipotassium glycyrrhizinate | 0.1 |
| Ascorbic acid glucoside | 2 |
| Tocopherol acetate | 0.1 |
| Cat's ear extract | 0.1 |
| Creeping saxifrage | 0.1 |
| Edetate trisodium | 0.1 |
| Xanthan gum | 0.3 |
| Alkyl acrylate/methacrylate copolymer (Pemulen TR-2) | 0.05 |
| Agar powder | 1.5 |
| Phenoxyethanol | Appropriate amount |
| Dibutylhydroxytoluene | Appropriate amount |
| Purified water | Balance |

(Preparation Method and Evaluation)

Following a conventional method, a semi-transparent emulsified composition was prepared and turned into gel by cooling the temperature down to 30° C. or lower; after the gel solidified sufficiently, a disper was used to crush and turn it into microgel (average particle size 70 μm) and deaerated to obtain a gel-like product. The obtained gel was refreshing, non-squeaky, and smooth, exhibiting good usability.

Example 39

Sunscreen Emulsion

| (Formulation) | (wt %) |
|---|---|
| Dimethylpolysiloxane | 5 |
| Decamethylcyclopentasiloxane | 25 |
| Compound of Synthesis example 4 | 2 |
| Trimethylsiloxysilicic acid | 5 |
| Polyoxyethylene-methylpolysiloxane copolymer | 2 |
| Ethyl ethylhexanoate | 5 |
| Dipropylene glycol | 5 |
| Dextrin palmitate-coated fine particle zinc oxide (60 nm) | 15 |
| Glutathione | 1 |
| Thiotaurine | 0.05 |
| Clara extract | 1 |
| Paraben | Appropriate amount |
| Phenoxyethanol | Appropriate amount |
| 2-ethylhexyl-p-methoxycinnamate | 7.5 |
| Dimethyl distearyl ammonium hectorite | 0.5 |
| Spherical poly alkyl acrylate powder | 5 |
| Butylethylpropanediol | 0.5 |
| Purified water | Balance |
| Perfume | Appropriate amount |

(Preparation Method and Evaluation)

The oil phase and the water phase were each mixed and dissolved. Dispersion of the powder in the oil phase was thoroughly conducted, to which the water phase was added, and emulsification was done using a homogenizer. The obtained sunscreen formulation exhibited a superior refreshing sensation.

Example 40

Sunscreen Emulsion

| (Formulation) | (wt %) |
|---|---|
| Dimethylpolysiloxane | 5 |
| Decamethylcyclopentasiloxane | 25 |
| Trimethylsiloxysilicic acid | 5 |
| Compound of Synthesis example 2 | 2 |
| Polyoxyethylene-methylpolysiloxane copolymer | 2 |
| Squalane | 5 |
| Dipropylene glycol | 5 |
| Fine particle zinc oxide (hydrophobicized product 60 nm) | 15 |
| Paraben | Appropriate amount |
| Phenoxyethanol | Appropriate amount |
| 2-ethylhexyl-paramethoxycinnamate | 7.5 |
| Dimethyl distearyl ammonium hectorite | 0.5 |
| Spherical poly alkyl acrylate powder | 5 |
| Purified water | Balance |
| Perfume | Appropriate amount |

(Preparation Method and Evaluation)

The oil phase and the water phase were each mixed and dissolved. Dispersion of the powder in the oil phase was thoroughly conducted, to which the water phase was added, and emulsification was done using a homogenizer. The obtained sunscreen had a low viscosity and was exceptionally refreshing.

Example 41

W/O Type Foundation

| | | |
|---|---|---|
| (1) Sericite | 5 | wt % |
| (2) Kaolin | 4 | |
| (3) Titanium dioxide | 6 | |
| (4) Red iron oxide | 0.36 | |
| (5) Yellow iron oxide | 0.8 | |
| (6) Black iron oxide | 0.16 | |
| (7) Aluminum stearate-treated titanium dioxide | 4 | |
| (8) Dextrin fatty acid-treated zinc oxide | 4 | |
| (9) Compound of Synthesis example 3 | 3 | |
| (10) Liquid paraffin | 5 | |
| (11) Decamethylcyclopentasiloxane | 29 | |
| (12) POE-modified dimethylpolysiloxane | 4 | |
| (13) Ion-exchanged water | 36 | |
| (14) 1,3-butylene glycol | 5 | |
| (15) Preservative | 0.1 | |
| (16) Perfume | 0.08 | |

(Preparation Method)

(7), (8), and (9) were dispersed and crushed with a beads mill, to which (1)-(6), (10) and (11) were added and mixed to obtain the oil phase. (12)-(15) were heated and dissolved at 70° C. and added to the oil phase, followed by emulsification. Additionally, (16) was added and mixed, and the product was put into a container.

Example 42

Oil Based Foundation

| (1) Talc | 14.3 wt % |
|---|---|
| (2) Kaolin | 10 |
| (3) Red iron oxide | 1 |
| (4) Dextrin fatty acid-treated yellow iron oxide | 3 |
| (5) Dextrin fatty acid-treated black iron oxide | 0.2 |
| (6) Dextrin fatty acid-treated titanium dioxide | 5 |
| (7) Dextrin fatty acid-treated zinc oxide | 5 |
| (8) Liquid paraffin | 20 |
| (9) Dimethylpolysiloxane | 15 |
| (10) Octylmethoxy cinnamate | 1 |
| (11) Sorbitan sesquiisostearate | 2 |
| (12) Isohexadecyl alcohol | 10 |
| (13) Ceresin | 4 |
| (14) Carnauba wax | 1 |
| (15) Compound of Synthesis example 1 | 3 |
| (16) Perfume | Appropriate amount |

(Preparation Method)

(8) and (10)-(14) were heated and mixed to obtain the oil phase. Separately, (6), (7), (9), and (15) were mixed and a beads mill was used to disperse and crush the mixture, which, along with (1)-(5), was then added to the oil phase and mixed with a disper. (16) was then mixed in and the mixture was put into a container and cooled.

Example 43

2-Layer Type W/O Sunscreen

| (1) Talc | 6 wt % |
|---|---|
| (2) Aluminum stearate-treated fine particle titanium dioxide | 6 |
| (3) Aluminum stearate-treated fine particle zinc dioxide | 10 |
| (4) Compound of Synthesis example 3 | 3 |
| (5) Liquid paraffin | 1 |
| (6) Decamethylcyclopentasiloxane | 30 |
| (7) Dimethylpolysiloxane | 20 |
| (8) POE-modified dimethylpolysiloxane | 2 |
| (9) Ion-exchanged water | 15 |
| (10) 1,3-butylene glycol | 8 |
| (11) Preservative | 0.1 |
| (12) Perfume | 0.1 |

(Preparation Method)

(5), (6), and (8) were heated and mixed at 70° C. to obtain the oil phase. Separately, (2)-(4) and (7) were mixed and a triple roller was used to knead the mixture. This kneaded mixture and (1) were added to the oil phase and mixed by using a disper. (9)-(11) were heated and dissolved at 70° C.

and added to this mixture, which was then emulsified, to which (12) was mixed in and the product was put into a container.

Example 44

Stick Type Sunscreen (Oil Based Cosmetic)

| (1) Talc | 3 wt % |
| --- | --- |
| (2) Kaolin | 10 |
| (3) Mica | 3 |
| (4) Aluminum palmitate-treated fine particle titanium dioxide | 25 |
| (5) Dimethylpolysiloxane | 20 |
| (6) Isopropyl palmitate | 13.9 |
| (7) Solid paraffin | 2 |
| (8) Microcrystalline wax | 3 |
| (9) Petrolatum | 10 |
| (10) Ceresin | 8 |
| (11) Carnauba wax | 1 |
| (12) Compound of Synthesis example 2 | 2 |
| (13) Perfume | 0.1 |

(Preparation Method)

(6)-(11) were heated and mixed at 90° C. to obtain the oil phase. Separately, (4), (5), and (12) were mixed and a triple roller was used to knead the mixture. This kneaded mixture and (1)-(3) were added to the oil phase and mixed by using a disper. (13) was then mixed in and the mixture was put into a container and cooled.

Example 45

Sun Cut Oil-in-Water Type Emulsion

| (1) Aluminum stearate-treated titanium dioxide | 5 wt% |
| --- | --- |
| (2) Dextrin stearate-treated zinc dioxide | 5 |
| (3) Compound of Synthesis example 1 | 3 |
| (4) Decamethylcyclopentasiloxane | 13 |
| (5) Octyl paramethoxycinnamate | 5 |
| (6) PEG-60 hydrogenated castor oil | 2 |
| (7) Dynamite glycerin | 6 |
| (8) Succinoglycan | 0.3 |
| (9) Carboxymethyl cellulose | 0.3 |
| (10) Ethanol | 5 |
| (11) Ion-exchanged water | Balance |

(Preparation Method and Evaluation)

(1)-(5) were mixed and a beads mill was used to disperse and crush the mixture, which was then added, as a homomixer was used, to the water phase prepared by dissolving (6)-(11). The obtained sun cut oil-in-water emulsion was refreshing and absorbed well into the skin, exhibiting a good tactile sensation during use.

Example 46

Oil-in-Water Type Emulsion Foundation

| (1) Aluminum palmitate-treated titanium dioxide | 5 wt % |
| --- | --- |
| (2) Aluminum palmitate-treated zinc dioxide | 5 |
| (3) Metal soap-treated talc | 3 |
| (4) Alkyl-modified silicone resin-coated yellow iron oxide | 0.8 |
| (5) Alkyl-modified silicone resin-coated black iron oxide | 0.16 |
| (6) Alkyl-modified silicone resin-coated red iron oxide | 0.36 |
| (7) Compound of Synthesis example 3 | 3 |
| (8) POE-modified methylpolysiloxane | 1 |
| (9) Decamethylcyclopentasiloxane | 15 |
| (10) Octyl paramethoxycinnamate | 5 |
| (11) PEG-60 hydrogenated castor oil | 2 |
| (12) Dynamite glycerin | 6 |
| (13) Xanthan gum | 0.3 |
| (14) Carboxymethyl cellulose | 0.3 |
| (15) Ethanol | 5 |
| (16) Ion-exchanged water | Balance |

(Preparation Method and Evaluation)

(1)-(10) were mixed and a beads mill was used to disperse and crush the mixture, which was then added, while a homomixer was used, to the water phase prepared by dissolving (11)-(16). The obtained foundation had no color mottling and gave an easy-to-spread, non-sticky, good tactile sensation during use.

Example 47

Ultraviolet Protection Whitening Essence (Oil-in-Water Type Emulsified Cosmetic)

| (1) Aluminum stearate-treated titanium dioxide | 5 wt % |
| --- | --- |
| (2) Aluminum stearate-treated zinc dioxide | 5 |
| (3) Compound of Synthesis example 2 | 3 |
| (4) Decamethylcyclopentasiloxane | 15 |
| (5) Octyl paramethoxycinnamate | 5 |
| (6) PEG-60 hydrogenated castor oil | 2 |
| (7) Dynamite glycerin | 6 |
| (8) Succinoglycan | 0.3 |
| (9) Carboxymethyl cellulose | 0.3 |
| (10) Ethanol | 6 |
| (11) Citric acid | Appropriate amount |
| (12) Sodium citrate | Appropriate amount |
| (13) Ascorbic acid glycoside | 2 |
| (14) Caustic potash | Appropriate amount |
| (15) Ion-exchanged water | Balance |

(Preparation Method and Evaluation)

(1)-(5) were mixed and a beads mill was used to disperse and crush the mixture, which was then added, while a homomixer was used, to the water phase prepared by dissolving (6)-(15). The obtained essence was smooth, easy-to-spread, and non-sticky, exhibiting a good tactile sensation during use.

INDUSTRIAL APPLICABILITY

The present invention can provide a cosmetic that is refreshing and at the same time absorbed into the skin very well. Also, the present invention can provide oil based cosmetics, water-in-oil type emulsified cosmetics, and oil-in-water type emulsified compositions that are superior in terms of the sensation during use and stability. Furthermore, the present invention can provide a powder dispersion cosmetic that has a very high powder dispersion stability and therefore exhibits excellent stability.

The invention claimed is:

1. A cosmetic comprising a triblock copolymer of glycerin modified on both ends with silicone according to formula (a):

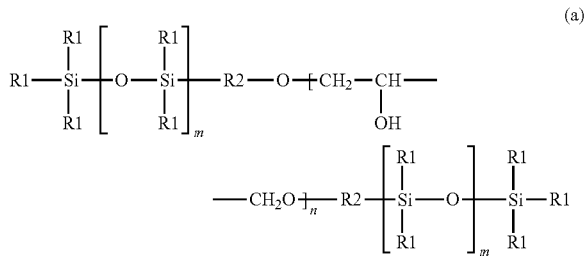

in which R1 denotes a straight chain or branched alkyl group having 1-12 carbon atoms or phenyl group, R2 denotes an alkylene group having 2-11 carbon atoms, m is 10-120, and n is 1-11.

2. The cosmetic of claim 1, wherein said cosmetic is an oil based cosmetic.

3. The cosmetic of claim 1, wherein said cosmetic is an water-in-oil emulsified cosmetic.

4. The cosmetic of claim 1, wherein said cosmetic is an oil-in-water emulsified composition.

5. The cosmetic of claim 1, wherein said cosmetic additionally contains powder.

6. The cosmetic of claim 2, wherein said cosmetic additionally contains powder.

7. The cosmetic of claim 3, wherein said cosmetic additionally contains powder.

8. The cosmetic of claim 4, wherein said cosmetic additionally contains powder.

9. A cosmetic comprising a triblock copolymer of glycerine modified on both ends with silicone according to formula (b):

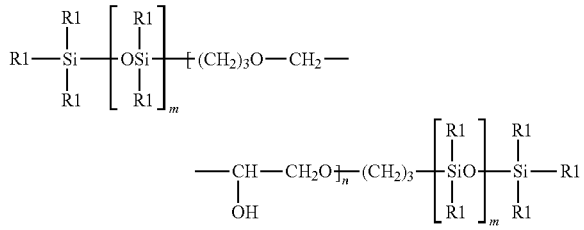

in which each R1 denotes a straight chain or branched alkyl group having 1-12 carbon atoms or a phenyl group, m denotes a number 10-120, and n denotes a number 1-11.

10. The cosmetic of claim 9, wherein said cosmetic is an oil based cosmetic.

11. The cosmetic of claim 9, wherein said cosmetic is an water-in-oil emulsified cosmetic.

12. The cosmetic of claim 9, wherein said cosmetic is an oil-in-water emulsified composition.

13. The cosmetic of claim 9, wherein said cosmetic additionally contains powder.

14. The cosmetic of claim 10, wherein said cosmetic additionally contains powder.

15. The cosmetic of claim 11, wherein said cosmetic additionally contains powder.

16. The cosmetic of claim 12, wherein said cosmetic additionally contains powder.

17. The cosmetic of claim 1, wherein the molecular weight of the triblock copolymer is between about 2,000-20,000.

18. The cosmetic of claim 9, wherein the molecular weight of the triblock copolymer is between about 2,000-20,000.

19. The cosmetic of claim 1, wherein in the triblock copolymer the blend ratio of glycerin modified on both ends with silicone is between about 0.1-50 wt %.

20. The cosmetic of claim 9, wherein in the triblock copolymer the blend ratio of glycerin modified on both ends with silicone is between about 0.1-50 wt %.

21. The cosmetic of claim 2, further comprising one or more oil components selected from the group consisting of chain polysiloxanes, cyclic polysiloxanes, modified siloxanes, epoxy-modified siloxane, and silicone resins.

22. The cosmetic of claim 10, further comprising one or more oil components selected from the group consisting of chain polysiloxanes, cyclic polysiloxanes, modified siloxanes, epoxy-modified siloxane, and silicone resins.

23. A method of forming a cosmetic with a stable powder dispersion, comprising:
mechanically dispersing a powder in a dispersion medium containing the triblock copolymer of claim 1.

24. A method of forming a cosmetic with a stable powder dispersion, comprising:
mechanically dispersing a powder in a dispersion medium containing the triblock copolymer of claim 9.

* * * * *